(12) United States Patent
Hu et al.

(10) Patent No.: US 8,481,728 B2
(45) Date of Patent: Jul. 9, 2013

(54) PROCESS FOR PREPARING ENTECAVIR AND ITS INTERMEDIATES

(75) Inventors: Tsung-Cheng Hu, Tainan (TW); Hung-Tsung Huang, Yunlin County (TW)

(73) Assignee: Scinopharm Taiwan, Ltd., Tainan (TW)

( * ) Notice: Subject to any disclaimer, the term of this patent is extended or adjusted under 35 U.S.C. 154(b) by 288 days.

(21) Appl. No.: 13/027,859

(22) Filed: Feb. 15, 2011

(65) Prior Publication Data

US 2011/0201809 A1    Aug. 18, 2011

Related U.S. Application Data

(60) Provisional application No. 61/305,039, filed on Feb. 16, 2010, provisional application No. 61/348,526, filed on May 26, 2010.

(51) Int. Cl.
*C07D 473/00* (2006.01)
*C07D 307/93* (2006.01)
*C07C 47/00* (2006.01)

(52) U.S. Cl.
USPC .............. 544/276; 549/465; 568/420

(58) Field of Classification Search
USPC ............ 560/255; 549/350, 370, 374; 544/276
See application file for complete search history.

(56) References Cited

U.S. PATENT DOCUMENTS

| 5,206,244 A | 4/1993 | Zahler et al. |
| 5,340,816 A | 8/1994 | Zahler et al. |
| 7,034,152 B2 | 4/2006 | Pendri et al. |
| 7,511,139 B2 | 3/2009 | Zhou et al. |
| 2007/0232064 A1 * | 10/2007 | Oh et al. ............ 438/675 |
| 2011/0288051 A1 * | 11/2011 | Li et al. ............ 514/63 |

FOREIGN PATENT DOCUMENTS

| CA | 2705953 A1 * | 11/2011 |
| WO | WO 2004/052310 | 6/2004 |
| WO | WO 2010/074534 | 7/2010 |

OTHER PUBLICATIONS

International Search Report for corresponding PCT Application No. PCT/SG2011/000066 Apr. 27, 2011.

* cited by examiner

*Primary Examiner* — Noble Jarrell
*Assistant Examiner* — Laura Daniel
(74) *Attorney, Agent, or Firm* — Enshan Hong; Kent H. Cheng; VLP Law Group LLP

(57) ABSTRACT

A process of making entecavir comprising converting a compound of formula (M5)

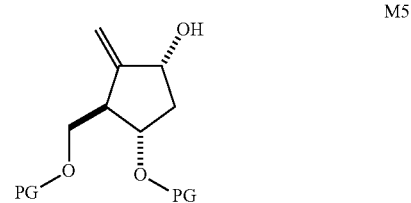

to entecavir,
wherein the two PGs on the formula (M5) are taken together to form an optionally substituted six- or seven-member cyclic ring.

17 Claims, No Drawings

PROCESS FOR PREPARING ENTECAVIR AND ITS INTERMEDIATES

RELATED APPLICATIONS

This application claims priority from U.S. Provisional Patent Application Ser. No. 61/305,039, which was filed on Feb. 16, 2010, and U.S. Provisional Patent Application Ser. No. 61/348,526, which was filed on May 26, 2010. The entire content of these two provisional patent applications is herein incorporated as reference.

BACKGROUND OF THE INVENTION

1. Field of the Invention

The present application relates to synthesis of entecavir and intermediates thereof.

2. Description of the Related Arts

Entecavir (Baraclude®) is a cyclopentyl guanosine nucleoside analogue, or called a novel carbocyclic 2'-deoxyguanosine analogue, which has shown potent and selective activity against Hepatitis B Virus (HBV). Entecavir was developed by Bristol-Myers Squibb (BMS) and it was approved by the United States Food and Drug Administration in March 2005. The chemical name of entecavir is 2-amino-1,9-dihydro-9-[(1S,3R,4S)-4-hydroxy-3-(hydroxymethyl)-2-methylenecyclopentyl]-6H-purin-6-one and is used as a mono hydrate form with molecular formula of $C_{12}H_{17}N_5O_4$, which corresponds to a molecular weight of 295.29 g/mol. Entecavir is a white to off-white powder, slightly soluble in water (2.4 mg/mL), and the pH of the saturated solution in water is 7.9 at 25° C.±0.5° C.

WO2004052310A2 (BMS patent application) discloses processes (see BMS Schemes 15 and 16, which are disclosed at pages 41 and 44 of WO2004052310A2 and shown below, hereinafter "BMS process") for the preparation of entecavir. WO2004052310A2 also discloses preparation of intermediates having silyl protecting groups by using Corey lactone as a starting material.

BMS SCHEME 15: A BMS entecavir synthesis route

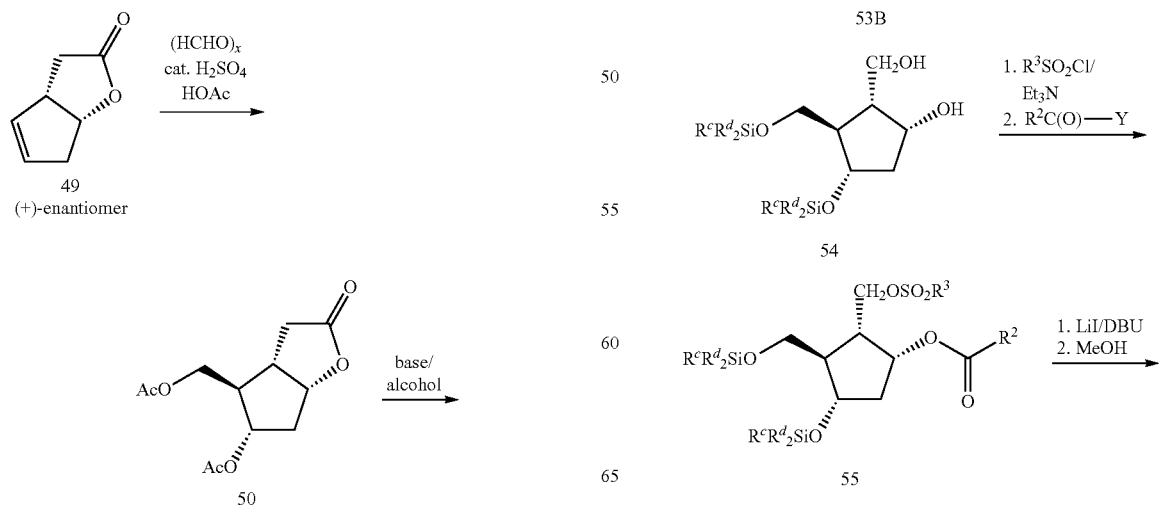

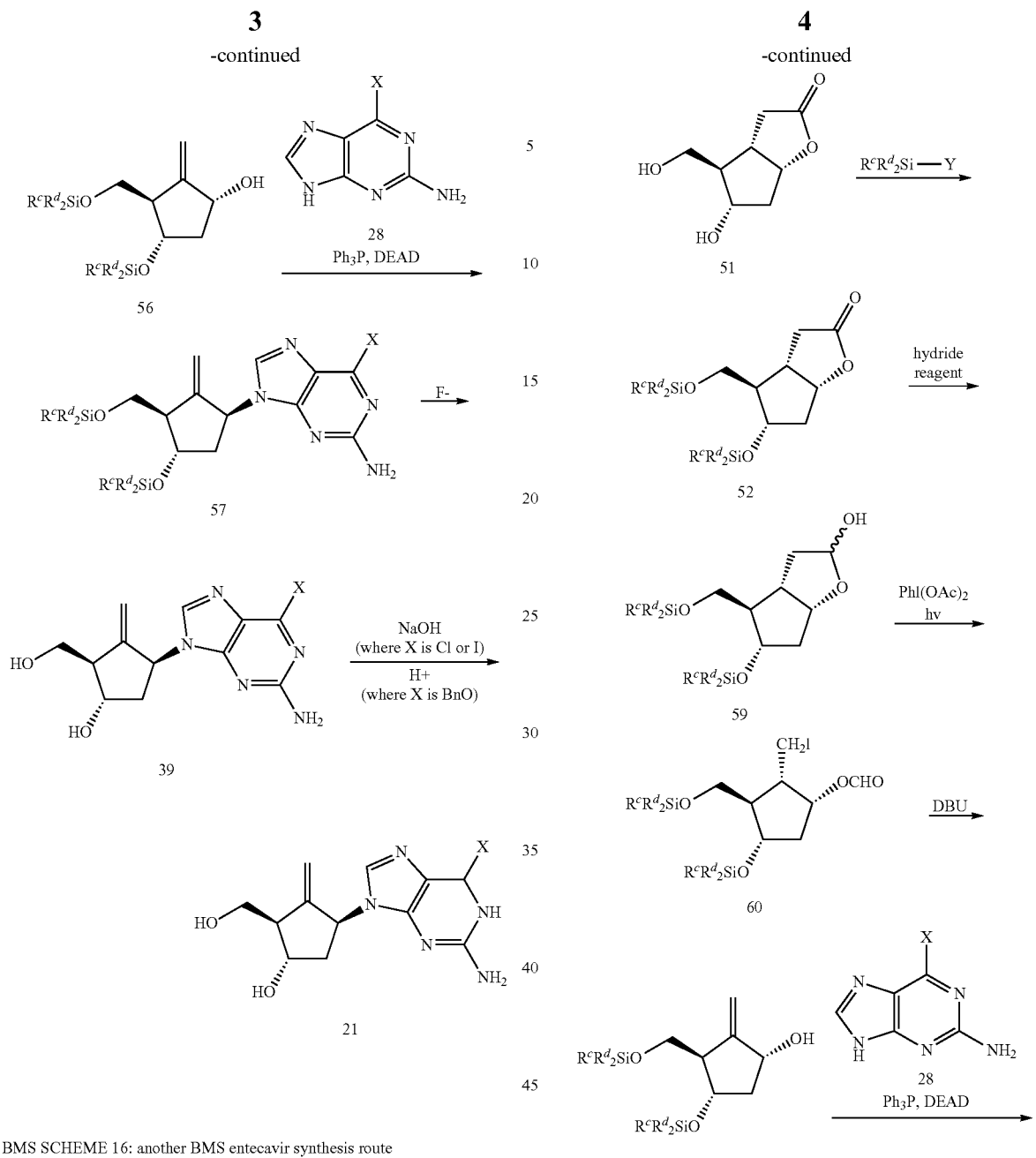
BMS SCHEME 16: another BMS entecavir synthesis route
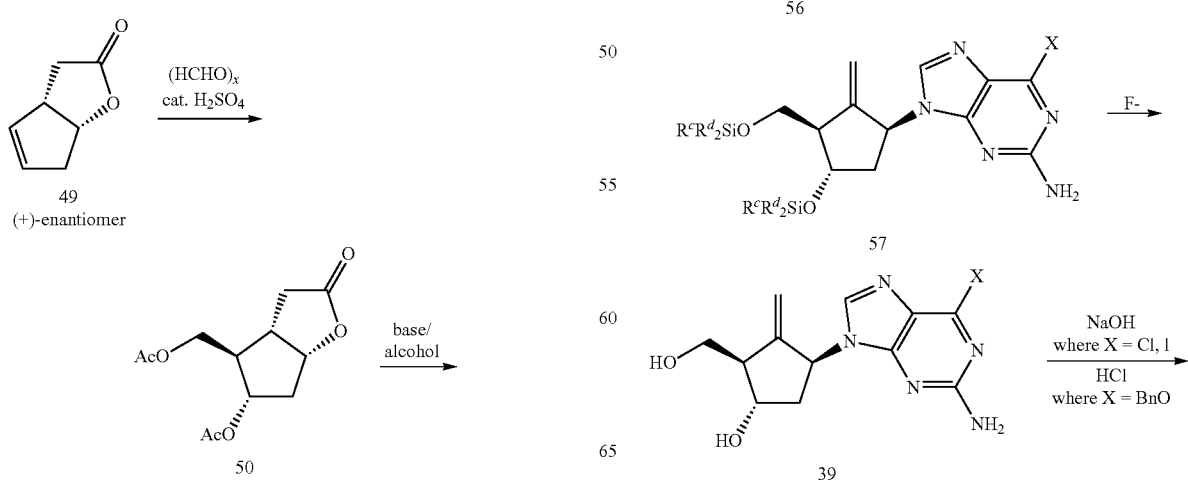

-continued

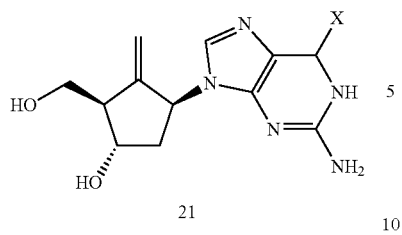

21

Despite prior disclosure of processes for the preparation of entecavir and intermediates thereof, there is still a need for a convenient process of making entecavir as well as its intermediates with desired purity and yield.

SUMMARY OF THE INVENTION

In accordance with one aspect of the present application, a process of making entecavir of the following formula:

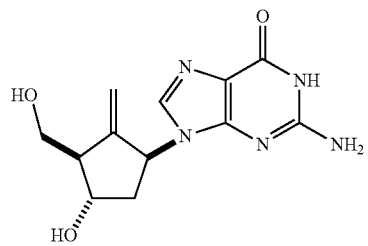 [SMILES: C=C1[C@H](CO)[C@@H](O)C[C@@H]1n1cnc2c(=O)[nH]c(N)nc21]

comprises converting a compound of formula (M5)

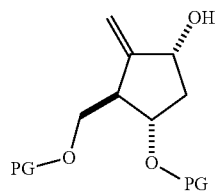

M5 to entecavir,
wherein the two PGs on the formula (M5) are taken together to form an optionally substituted six- or seven-member cyclic ring. Preferably, the compound of formula (M5) may be a compound with one of the following formulae:

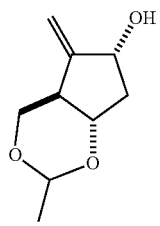 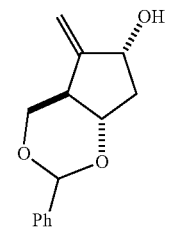 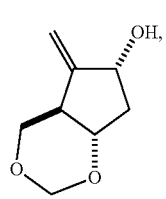

Ethylidene    Phenylmethylidene    Methylidene and more preferably, the compound of formula (M5) is

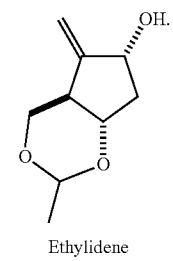

Ethylidene

The step of converting a compound of formula (M5) to entecavir may comprise:

reacting the compound of formula (M5) with a compound of formula (A):

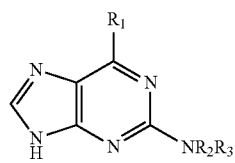

(A)

to give a compound of formula (M6):

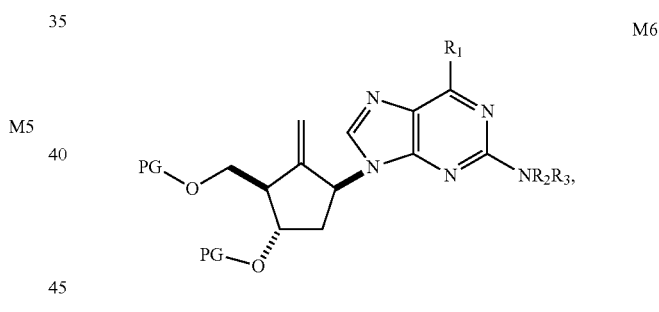

M6 wherein $R_1$ is halogen, alkyl (preferably C1-C6), cycloalkyl (preferably C1-C6), aralkyl (preferably C1-C6), aryl (preferably C1-C6), alkoxy (preferably C1-C6), thioalkyl (preferably C1-C6), thio, or hydroxyl; $R_2$ and $R_3$ are independently defined as H or an amino protecting group; and de-protecting the compound of formula (M6) to obtain entecavir.

The reaction of the compound of formula (M5) and the compound of formula (A) to make the compound of formula (M6) may be a Mitsunobu reaction carried out in the presence of a reagent selected from the group consisting of diethyl azodicarboxylate (DEAD), diisopropyl azodicarboxylate (DIAD), and combination thereof, a trisubstituted phosphine, and an organic solvent.

The compound of formula (M6) may be isolated from a mixture formed from the reaction of the compound of formula (M5) and the compound of formula (A) by crystallization.

The above-mentioned compound of formula (A)

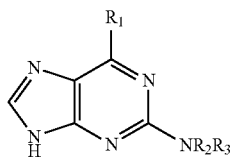

may be prepared by a method comprising;
reacting a 6-substituted purine compound of formula

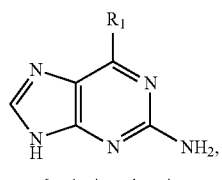

6-substituted purine wherein $R_1$ is as defined above in connection with the compound of formula (A), with an amino protecting reagent, such as di-t-butyl-dicarbonate ($Boc_2O$), in an organic solvent at a temperature of from −60° C. to about reflux to yield the compound of formula (A). Preferably, $R_1$ is halogen, more preferably, $R_1$ is.

The compound of formula (M5) discussed above may be prepared by a method comprising:
(a) reducing a compound of formula (M1):

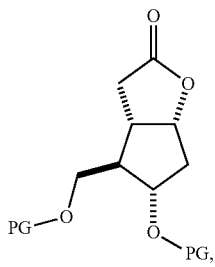

to give a compound of formula (M2):

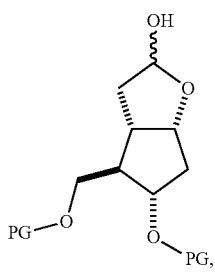

wherein each of the PGs on formulae (M1) and (M2) is as defined above concerning the formula (M5); and
(b) converting the compound of formula (M2) to give the compound of formula (M5).

The compound of formula (M5) may be isolated from a mixture resulted from the converting step (b) by crystallization.

The compound of formula (M5) may be prepared from the compound of formula (M2) by a method comprising the following steps:
oxidizing the compound of formula (M2) to obtain a compound of formula (IM1)

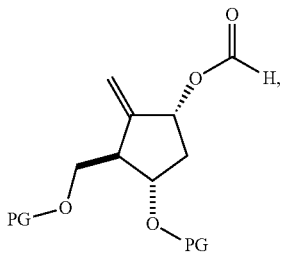

wherein each of the PGs on the formula (IM1) is as defined above concerning the formula (M5); and converting the compound of formula (IM1) to the compound of formula (M5).

The compound of formula (M5) may also be prepared from compound of formula (M2) by a process comprising:
dehydrating the compound of formula (M2) to provide a compound of formula (M3);

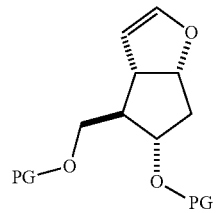

oxidizing the compound of formula (M3) to obtain a compound of formula (M3IM)

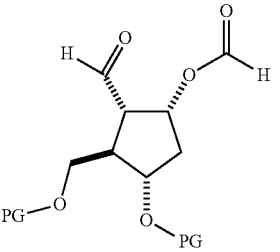

and
reducing the compound of formula M3IM obtained from the oxidizing step to provide a compound of formula (M4)

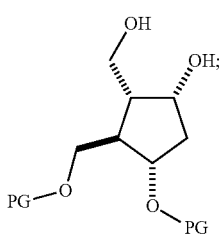

M4 and deyhydrating the compound of formula (M4) to the compound of formula (M5);

wherein each of the PGs on the formulae (M3 and M4) is independently as defined above concerning the compound of formula (M5).

The step of dehydrating the compound of formula (M4) to the compound of formula (M5) may comprise:

converting the compound of formula (M4) to give a protected compound of formula (M5a):

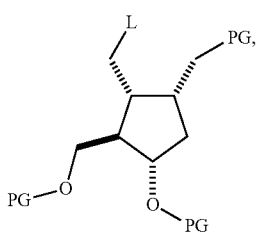

M5a wherein L is a leaving group;

removing the leaving group of the protected compound of formula (M5a) to give a compound of formula (M5b):

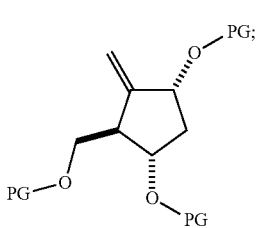

M5b and de-protecting the compound of formula (M5b) to obtain the compound of formula (M5);

wherein each of the PGs on the formulae (M5a) and (M5b) is independently as defined above concerning the compound of formula (M5).

The compound of formula (M1) may be prepared by converting (+)-Corey dial of formula

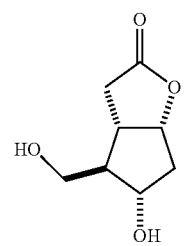

(+)-Corey diol to the compound of formula (M1).

The process in accordance with an embodiment of the present application may comprises a step of isolating the compound of formula (M1) from a mixture resulted from the reaction of converting (+)-Corey dial to the compound of formula (M1) by crystallization.

In accordance with another aspect of the present application, a process for preparing a compound of formula

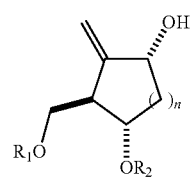

(5)

comprises:
oxidizing a compound of formula (2):

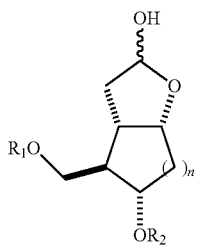

(2)

to provide an intermediate of formula (IM2):

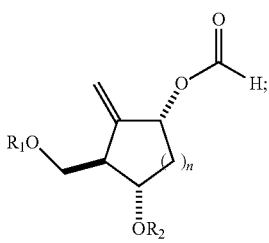

IM2 and
converting the intermediate of formula (IM2) to the compound of formula (5);

wherein $R_1$ and $R_2$ each is independently a hydroxy protecting group; or $R_1$ and $R_2$ are taken together to form an optionally substituted six- or seven-member cyclic ring; n is 1 to 3.

For example, the optionally substituted six- or seven-member cyclic ring may be a cyclic acetal (ethylidene), cyclic ketal (isopropylidene), or cyclic ether, or a cyclic ester.

The step of converting the intermediate of formula (IM2) to the compound of formula (5) may comprise hydrolyzing the intermediate of formula (IM2).

The step of oxidizing and the step of converting the intermediate of formula (IM2) to the compound of formula (5) may be carried out in one pot.

The compound of formula (5) may be further converted to an antiviral drug, preferably entecavir.

The oxidizing step may be carried out in the presence of an oxidizing agent selected from the group consisting of $Pb(OAc)_4/CuCl_2$, $PhI(OAc)_2$ (iodobenzene diacetate)/$CuCl_2$, $Pb(OAc)_4/CuBr_2$, $PhI(OAc)_2/CuBr_2$, $Pb(OAc)_4/CuI_2$, $PhI(OAc)_2/CuI_2$, $Pb(OAc)_4/CuSO_4$, $PhI(OAc)_2/CuSO_4$, $I_2/AIBN$, $PbI(OAc)_2/I_2/AIBN$, $Mn(OAc)_3$, ceric ammonium nitrate (CAN), $Fe(OAc)_3$, $PhI(OAc)_2$, Dess-Martin periodinane (DMP), 2-Iodoxybenzoic acid (IBX), and combinations thereof.

In accordance another aspect of the present application, a compound of formula (IM1):

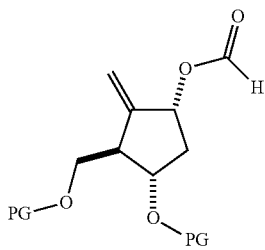

IM1 wherein each of the PGs is independently a hydroxy protecting group, or taken together to form an optionally substituted six- or seven-member cyclic ring, is provided.

In accordance yet with another aspect of the present application, compounds of the following formulae are provided:

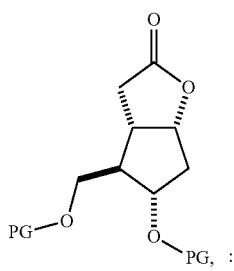

M1

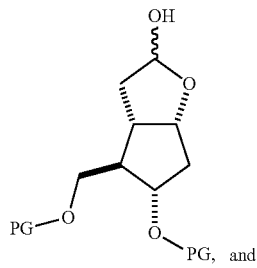

M2

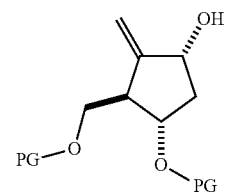

M5 wherein the two PGs on the formula (M5) are taken together to form an optionally substituted six- or seven-member cyclic ring, or each of the PGs on the formula (M1), (M2) and (M5) independently represents a hydroxyl protecting group selected from the group consisting of tert-butyldimethylsilyl and optionally substituted triphenylmethyl, alkoxymethyl, and arylalkoxymethyl.

Other objects and features of the present invention will become apparent from the following detailed description.

DETAILED DESCRIPTION OF THE PRESENTLY PREFERRED EMBODIMENTS

The following preferred embodiments are presented to further illustrate the invention but of course, should not be construed as in any way to limit its scope.

As used herein, the term "leaving groups" generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

A "hydroxy protecting group" used herein refers to those groups intended to protect a hydroxyl group against undesirable reactions during synthetic procedures. For example, the hydroxyl protecting groups include alkyl, cycloalkyl, arylalkyl, aryl, ethers, esters, cyclic ethers, cyclic esters, cyclic acetal, and cylic ketal.

An "amino protecting group" used herein refers to those groups intended to protect an amino group against undesirable reactions during synthetic procedures. For example, the amino protecting group can be carbamates, amides, N-Alkyl and N-aryl amines and N-sulfonyl derivatives. Boc is a preferred amino protecting group.

One-pot synthesis discussed herein is a strategy to improve the efficiency of a chemical reaction whereby a reactant is subjected to successive chemical reactions in just one reactor. For example, as discussed above, in accordance with one embodiment of the present application, we can combine two operations (2)→IM2→(5) into one step operation (2)→(5).

Our synthetic process route to entecavir and its intermediates starts from commercial Corey lactone diol (also referred hereinafter as "Corey diol") as shown in SPT Scheme 1 below.

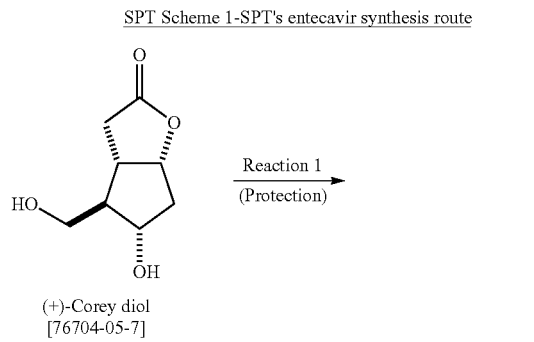

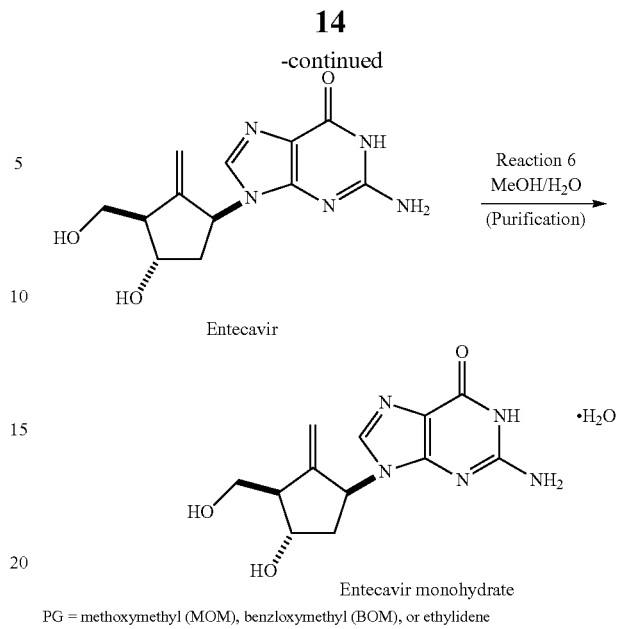

PG = methoxymethyl (MOM), benzloxymethyl (BOM), or ethylidene

SPT Scheme 1 is substantially different from BMS Scheme 16. In our SPT route, the Corey diol is separately treated with dimethoxymethane, benzyl chloromethyl ether, or acetaldehyde diethyl acetal to give the M1 series with different protecting groups: methoxymethyl (MOM), benzyloxymethyl (BOM), and ethylidene. When ethylidene protection was used, M1 was isolated as a crystalline solid, with a high yield (e.g., about 90%). Acetaldehyde diethyl acetal, which is relatively cheap, may be used as a hydroxyl protecting reagent to react with (+)-Corey diol at an appropriate temperature to produce M1. Trace $NaHCO_3$ may be used during the work-up. By contrast, BMS's corresponding silyl ether protected analogue 52 is obtained in form of oil, which means column chromatography is required for purification. Silyated reagent, which is more expensive, is needed. The silyation reaction needs to be carried out for as long as 14 hours. During work-up, 1.0N hydrochloric acid, 1.0N sodium hydroxide, and brine are needed. The yield is relative low (e.g., 82%).

Then, our lactone to lactol reduction (i.e., M1→M2) is achieved using DIBAL (diisobutylaluminium hydride) at a low temperature (below −40° C.) to afford crystalline M2 in quantitative yield as a diastereomeric mixture. The reaction is relatively fast (e.g., 1 hour). Methanol and water may be used during the work-up. An organic solvent may be used to facilitate the crystallization of M2. The yield is relatively high (e.g., 90%).

Using either of two insert modules (i.e., module 1: hydrolysis or alcholysis; module 2: oxidiative cleavage), key intermediated M5 (e.g., ethylidene protection) may be obtained as a crystalline solid. By contrast, BMS's corresponding silyl ether protected analogue 56 is an oil.

For module 1 (see SPT Scheme 2 below), the pathway includes dehydration, ozonolysis/reduction and elimination to provide M5. In contrast to module 1, module 2 was more efficient and provided higher throughput (SPT Scheme 3) and this is therefore preferred over module 1. Module 2 utilizes an oxidative cleavage reaction that was explored by professor Rigby for oxidative cleavage of lactols unrelated to entecavir. We found that by treating M2 with $Pb(OAc)_4$ and $Cu(OAc)_2$ in a selected solvent, M2 directly underwent fragmentation to give a crystalline intermediate IM1. Subsequent hydrolysis or alcoholysis of the intermediate IM1 gave the desired crystalline M5. Moreover, we were able to combine the two steps into a one-pot procedure to afford crystalline M5 in a similar yield. In 1967 Oyo Mitsunobu reported the reaction of alcohols and carboxylic acids in the presence of diethyl azodicarboxylate (DEAD) and triphenylphosphine (TPP) to give the corresponding esters in high yield. More recently, the Mitsunobu reaction has been widely used in asymmetric synthesis and in industry. However, when this reaction was applied to the synthesis of M6, it led to many side products that needed to be removed from the product M6. To address this purity issue, we developed a purification process that relied on the crystallization of M6 giving high quality product. A Mitsunobu reaction between M5 and N2-Boc-2-amino-6-iodopurine (the preparation method was shown above in SPT Scheme 1) were carried out in the presence of DEAD (or DIAD) and TPP in the specific solvent to afford crystalline M6 in about 70% yield. Dichloromethane may be used as a solvent during the Mitsunobu reaction. We preferred to use the 6-iodopurine system in contrast to other C6-substituted derivatives because the iodo substituent provided better regio-selectivity for the N9-isomer versus the unwanted N7-isomer due to the iodide steric effect. The Mitusunobu reaction in accordance with an embodiment of the present application may be carried out at room temperature for about 1 hour. Work-up can be achieved by filtering and extracting. By contrast, the BMS process could not isolate compound 57, which corresponds to M6 of the present application, through crystallization, because BMS' compound 57 was an oil. Column chromatography needs to be used in the BMS' process. The yield in the BMS' process is relatively low (eg, 63%). The Mitusnobu reaction of the corresponding BMS' process was carried out in the presence of DEAD, TTP, and THF (as a solvent) at −20° C.

Finally, M6 (e.g., ethylidene protection) was converted to entecavir with high reactivity in the presence of aqueous TFA solution or other aqueous organic/inorganic acid solutions. After purification, the desired entecavir monohydrate was obtained with high quality in high yield. The use of crystalline intermediates within our synthetic process for entecavir allows the manufacture of high quality API since the quality can be controlled at the various intermediates. This reaction may be carried out at 70° C. for about 1 hour. Two steps, namely, neutralization (e.g., using TFA) and extraction, may be needed in making entecavir monohydrate from M6. The yield is relatively high (e.g., 70%). The purification of entecavir monohydrate may be conducted through crystallization from water and methanol. In contrast, in BMS' process, three steps are needed to make entecavir monohydrate from BMS's compound 57, which corresponds to M6 of the present application, and the yield is relatively low (32.4%).

SPT Synthesis of N2-Boc-2-amino-6-iodopurine

2-Amino-6-chloropurine

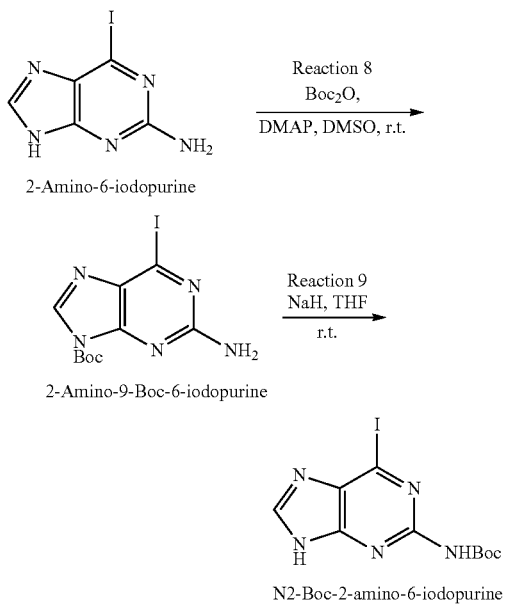

2-Amino-6-iodopurine

Reaction 8
Boc₂O,
DMAP, DMSO, r.t.

2-Amino-9-Boc-6-iodopurine

Reaction 9
NaH, THF
r.t.

N2-Boc-2-amino-6-iodopurine

SPT SCHEME 2: Insert module 1 for M2 to M5

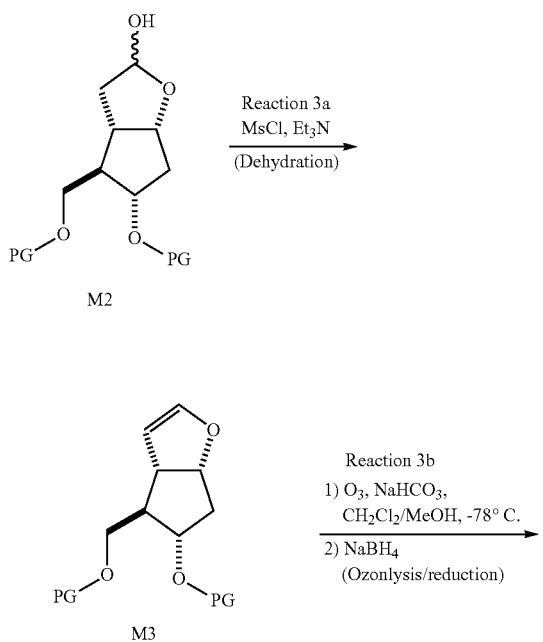

M2

Reaction 3a
MsCl, Et₃N
(Dehydration)

M3

Reaction 3b
1) O₃, NaHCO₃,
   CH₂Cl₂/MeOH, −78° C.
2) NaBH₄
(Ozonlysis/reduction)

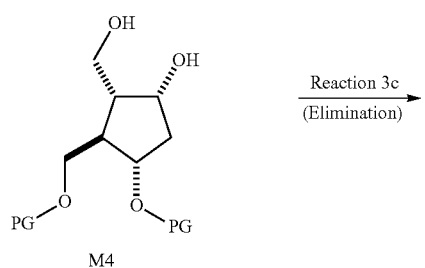

M4

Reaction 3c
(Elimination)

-continued

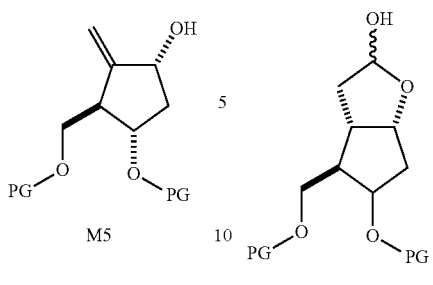

M5

SPT SCHEME 3: Insert module 2 for M2 to M5

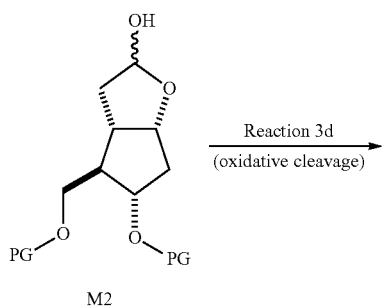

M2

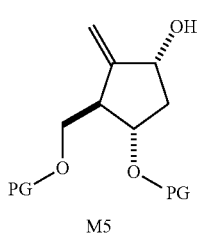

M5

Different Intermediates of BMS and SPT Process:

BMS 59→56:

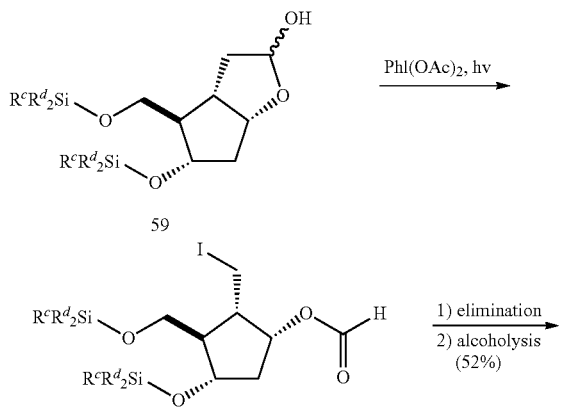

SPT M2→M5:

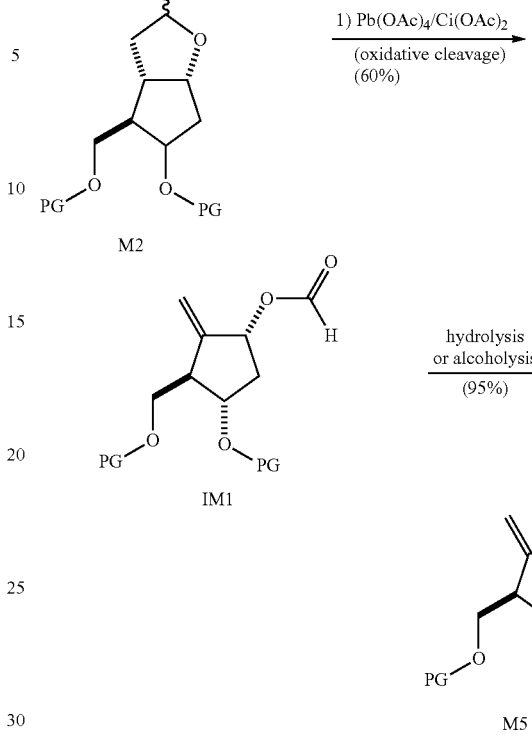

As shown above, compared to the BMS process, the process in accordance with an embodiment of the present application has the following characteristics and advantages:

1. The present application provides a cost effective access process of making high grade of entecavir product, which suitable for human consumption, by utilizing commercially available "Corey's diol"-as a key, stereochemically rich starting material.

2. The synthetic route provided in the present application can be preformed using any three hydroxy protecting groups: MOM, BOM and ethylidene. (BOM and ethylidene are superior to MOM and provide a higher overall yield. Ethylidene is superior to BOM since the intermediates are crystalline which allows good quality control of intermediates and the product by crystallization which is an efficient purification method on a manufacturing scale. Therefore, for API manufacturing, the ethylidene protecting group is preferred.)

3. The same general synthetic route can be used for all protecting groups. During our development, we devised a $1^{st}$ and $2^{nd}$ generation approach to common intermediates M2 to M5, which we refer to as insert Module 1 and 2, respectively, Corey dial to M2 (Reaction 1 and 2), and M5 to entecavir (Reaction 4, 5 and 6) are essentially the same for all synthetic route variants.

4. Insert module 1 (M2 to M5; Reaction 3) was demonstrated for MOM and BOM protecting groups and uses the longer "dehydration/ozonolysis/elimination" protocol.

5. Insert module 2 (M2 to M5; Reaction 3) was demonstrated for BOM and ethylidine protecting groups and uses the shorter "oxidative cleavage" protocol.

6. Although the overall yield might be similar for module 1 and 2, module 2 is probably advantageous because it saves about twelve operation steps and therefore would be much more time and reagent efficient.

7. We developed a process that utilizes novel intermediates with crystalline properties. Without column chromatography purification, we could make high quality intermediates by crystallization. Crystallization is more convenient, efficient, environmentally friendly, time and cost efficient than column purification in the production plant. We have utilized the crystalline property of ethylidene derivatives of M1, M2, M5, M6 to control quality throughout the synthesis by crystallization/precipitation.

8. The differences between the process in accordance with an embodiment of the present application and BMS's synthetic route (see BMS Scheme 16) include: 1) crystalline intermediates instead of non-crystalline intermediates are used in the process in accordance with an embodiment of the present application, and 2) in an embodiment of the present application, a different process of converting M2 to M5 is used, in comparison with BMS's scheme of converting compound 59 to compound 56 (see BMS Scheme 16). For the preparation of key intermediate M5, instead of using photo irradiation to convert compound 59 to compound 60 in BMS's Scheme 16, we developed a scalable reaction process to produce high quality M5 with about 60% yield over two steps.

9. The method in accordance with the present application provides higher throughput, a more simple operation, and greater efficiency than BMS's method.

10. For the Mitsunobu reaction in M5 to M6 (Reaction 4), we utilized a crystalline product M6 (in comparison with BMS's oily compound 571) and convenient and efficient conditions to isolate the M6 with high purity. The crystallization and isolation of M6 was very convenient because we simply added MeOH as anti-solvent during solvent swap from the dichloromethane reaction solvent providing M6 as a slurry phenomenon and subsequently the solid is filtered to obtain the desired product.

11. For M6 to entecavir (reaction 5), the process in accordance with an embodiment of the present application only requires two steps to isolate the product. In contrast, BMS patent application reports a complicated method to afford entecavir that utilizes resin catch/release purification.

12. In accordance with an embodiment of the present application, only six overall synthetic steps are needed to prepare entecavir; whereas eight steps are needed in BMS's process.

EXAMPLES

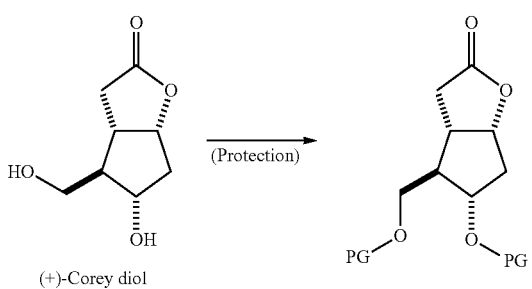

Example 1

Reaction 1

Preparation of (3aS,4R,5S,6aR)-hexahydro-5-(methoxymethoxy)-4-((methoxymethoxy)methyl)cyclopenta[b]furan-2-one (M1 with MOM protection)

To a stirred suspension of Corey diol (20 g, 0.116 mol, 1.0 eq), p-TSA (28.69 g, 0.151 mol, 1.3 eq) and dimethoxymethane (150 mL) was stirred for 2 hr at room temperature. Upon completion, the solvent is concentrated through vacuum. Then water and dichloromethane was added for extraction. The lower organic layer was concentrated to dryness to afford a crude oil. The oil is purification via column chromatography to afford colorless oil. Yield: 12.4 g (60%).

$^1$H NMR (400 MHz, CDCl$_3$) δ4.84 (s, 1H), 4.47 (m, 4H), 3.90 (m, 1H), 3.33 (m, 2H), 3.22 (m, 6H), 2.64 (m, 2H), 2.37 (m, 1H), 2.17 (m, 3H).

Example 2

Reaction 1

Preparation of (3aS,4R,5S,6aR)-5-((benzyloxy)methoxy)-4-(((benzyloxy)methoxy)methyl)-hexahydrocyclopentafuran-2-one (M1 with BOM protection)

To a stirred suspension of Corey diol (20 g, 0.116 mol), N,N-diisopropylethylamine (150.0 g, 1.16 mol; 10 eq), tetrabutylammonium iodide (34.32 g, 0.093 mol, 0.8 eq) and dichloromethane (140 mL, 7 parts) was stirred. Subsequently, benzyl chloromethyl ether (145.3 g, 0.928 mol, 8 eq) was added slowly below 20° C. and the mixture was stirred at room temperature after 3 h for the completion, the 2N HCl aqueous solution (150 mL) was added slowly below 20° C. Then ethyl acetate (200 mL) was added for extraction and the aqueous layer was washed with ethyl acetate twice. The combined organic layer was washed with brine/saturated sodium bicarbonate solution (50 mL/50 mL) and the organic layer was washed with water (100 mL). The organic layer was dried over MgSO$_4$ and concentrated to dryness to afford a crude oil (68.2 g).

$^1$H NMR (400 MHz, CDCl$_3$) δ7.36 (m, 10H), 4.98 (m, 1H), 4.78 (m, 4H), 4.62 (m, 4H), 4.10 (m, 1H), 3.52 (m, 2H), 2.83 (m, 1H), 2.71 (m, 1H), 2.56 (m, 1H), 2.24 (m, 3H).

Example 3

Reaction 1

A Preparation of M1 with Ethylidene Protection

Charge (+)-corey diol (19.98 kg, 1.0 eq), of p-toluenesulfonic acid monohydrate (0.53 Kg, 0.03 eq) and 2-methyl-THF (206.35 kg) into a suitable vessel under nitrogen and the mixture was stirred at below 35° C. Then charge acetaldehyde diethyl acetal (16.00 kg, 1.5 eq) into the reaction mixture under nitrogen and stirred at reflux for about 1 h.

After completion, about 5% NaHCO$_3$ aqueous solution 120% brine (about 37.2 kg, Prepare: 2.15 kg NaHCO$_3$+11.45 kg NaCl+87.4 kg SPW) was added into the reaction mixture at below 35° C. and settle for phase separation. After phase separation, the organic phase is collected and the aqueous layer is continued to extract with dichloromethane (28.1 kg). After phase separation, the dichloromethane layer is collected and combined with the previous organic layer. Then reduce the solvent by distillation until cloudy. Subsequently, n-heptane (32.8 kg) is charged at about 40° C. The resultant slurry is cooling to −5 to 10° C. and stirred for about 1 h. The solids were filtered, washed with a cold (−5 to 10° C.) co-solvent containing 2-methyl THF/n-heptane (13.7 kg/10.9 kg). The wet cake was dried under vacuum at 60° C. to afford crystalline M1 (~20.0 Kg). Yield: about 90%. $^1$H NMR (400 MHz, CDCl$_3$) δ 4.88 (m, 1H), 4.68 (m, 1H), 4.25 (m, 1H), 3.58-3.37 (m, 2H), 2.71-1.64 (m, 6H), 1.33 (s, 3H).

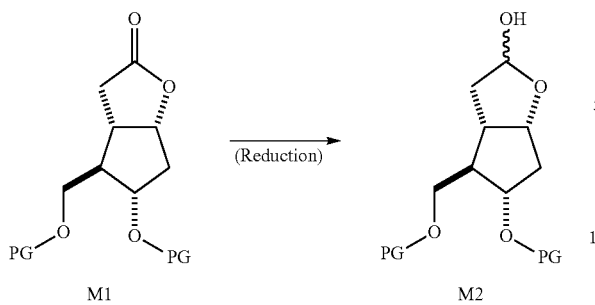

Example 4

Reaction 2

Preparation of (3aS,4R,5S,6aR)-hexahydro-5-(methoxymethoxy)-4-((methoxymethoxy)methyl)-2H-cyclopenta[b]furan-2-ol (M2 with MOM protection)

A solution of DIBAL in toluene (70 mL of 1.2M in toluene) was added during 30 min at −78° C. to a stirred solution of M1 (12.35 g, 47.45 mmol) in THF under nitrogen. The mixture was stirred for 1 hour at −70 to −60° C. and the reaction quenched by addition of methanol (25 mL). After warming to 0° C., water was added dropwise and the mixture was stirred for 1.5 hr. The solid was filtered and washed with ethyl acetate. The combined organic layer is washed with saturated sodium chloride. The organic layer is collected and dried over anhydrous magnesium sulfate. Evaporation of the solvent gave a crude oil. The oil is purification via column chromatography to afford colorless oil (dr=1:1). Yield: 12.2 g (90%). $^1$H NMR (400 MHz, CDCl$_3$) δ5.66 (s, 1H), 5.64 (m, 1H), 4.60 (m, 4H), 4.00 (m, 1H), 3.97 (m, 1H), 3.50 (m, 4H), 3.40 (m, 12H), 3.37 (m, OH), 2.60-1.83 (m, 10H).

Example 5

Reaction 2

Preparation of (3aS,4R,5S,6aR)-5-((benzyloxy)methoxy)-4-(((benzyloxy)methoxy)methyl)-hexahydro-2H-cyclopentafuran-2-ol (M2 with BOM protection)

A solution of DIBAL in THF (73 mL of 1.0M in THF; 2 eq) was added during 30 min below −55° C. to a stirred solution of M1 (15 g, 36.4 mmol) in THF (105 mL; 7 parts) under nitrogen. The mixture was stirred for 1 hour below −55° C. and the reaction quenched by addition of Methanol (45 mL; 3 parts). After warming to 0° C., water (90 mL) was added drop-wise and the mixture was stirred at about 2 hr. The solid was filtered and washed with ethyl acetate (50 mL). The filtrate was removed about a half volume of solvent. The phase was separated and the aqueous layer was washed with Ethyl acetate (50 mL×2). The combined organic layer is washed with saturated sodium chloride (100 mL). The organic layer is collected and dried over anhydrous magnesium sulfate. Evaporation of the solvent gave a crude oil (21 g). $^1$H NMR (400 MHz, CDCl$_3$) δ7.36 (m, 10H), 5.68 (m, 1H), 5.50 (m, 1H), 4.8-4.5 (m, 10H), 4.09-4.07 (m, 2H), 3.56 (m, 4H), 2.6-2.07 (m, 12H).

Example 6

Reaction 2

A Preparation of M2 with Ethylidene

Charge M1 (1.22 k g, 1.0 eq) and toluene (10.85 kg) into a suitable vessel under nitrogen and the solution is cooled to below −45° C. Then, DIBAL solution (9.465 kg, 1.0 M in toluene, about 1.5-1.6 eq) was charged into the solution at below −45° C. for about 0.5 h. After completion, the reaction is quenched by addition of methanol (2.3 kg) and then stirred at below −45° C. for about 0.5 h. Subsequently, water (2.94 kg) was added drop-wise at below 35° C. and the mixture was stirred for about 5 h. The solid was filtered and washed with MeOH (5.82 kg) and toluene (2.62 kg). The filtrate was collected and reduced solvent by distillation at until the suitable volume. Subsequently, the mixture is seeded with M2 seed (0.002 kg) until cloud point is observed. The mixture is cooled to −5 to 10° C., and the solid is filtered and washed with cold n-heptane (2.02 kg). The wet cake is dried at below 60° C. under vacuum to afford M2 (about 1.327 kg). Yield: about 85-95%. $^1$H NMR (400 MHz, CDCl$_3$) δ 5.6 (m, 1H), 4.6 (m, 2H), 4.18 (m, 2H), 3.47 (m, 1H), 3.32 (m, 1H), 2.47-1.54 (m, 5H), 1.30 (m, 3H).

Module 1: M2 to M4 steps

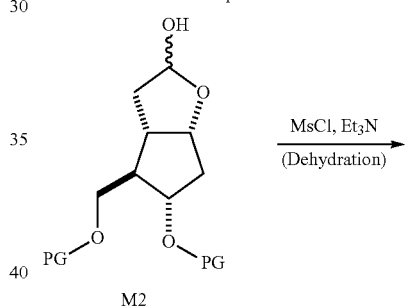

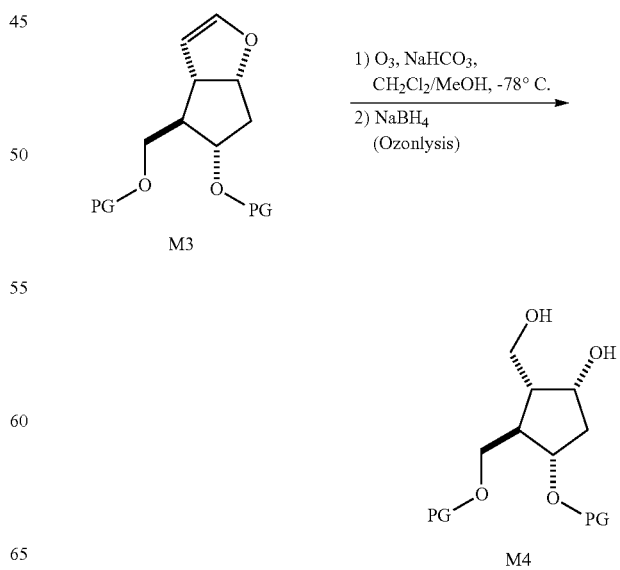

Example 7

Reaction 3a

Preparation of (3aS,4R,5S,6aR)-4,5,6,6a-tetrahydro-5-(methoxymethoxy)-4-((methoxy-methoxy)methyl)-3aH-cyclopenta[b]furan (M3 with MOM protection)

To a stirred solution of M2 (12.2 g, 0.075 mol, 1.0 eq) and Et$_3$N (28.3 g, 0.279 mol, 3.72 eq) in THF (60 mL) was stirred for 30 min at −60 to −70° C. Then MsCl (10.7 g) is added into the solution and stirred at −60 to −70° C. for about 1 hour. Upon completion, the mixture is warmed and heated to reflux for about 3 hr. After completion, water and ethyl acetate was added for extraction about two times. The organic layer was combined and concentrated to dryness to afford a crude oil. The oil is purification via column chromatography to afford colorless oil. Yield: 11.4 g (90%). $^1$H NMR (400 MHz, CDCl$_3$) δ6.25 (d, 1H), 5.05 (m, 1H), 4.92 (m, 1H), 4.66 (m, 4H), 3.90 (m, 1H), 3.57 (m, 2H), 3.37 (m, 6H), 3.12 (m, 1H), 2.52 (m, 1H), 2.15 (m, 1H), 1.99 (m, 1H).

Example 8

Reaction 3a

Preparation of (3aS,4R,5S,6aR)-5-((benzyloxy)methoxy)-4-(((benzyloxy)methoxy)methyl)-4,5,6,6a-tetrahydro-3aH-cyclopentafuran (M3 with BOM protection)

To a stirred solution of M2 (21 g, 0.05 mol, 1.0 eq) and triethylamine (17.4 g, 0.17 mol, 3.4 eq) in THF (71 mL) was stirred for 30 min at −60 to −70° C. Then Methanesulfonyl chloride (6.56 g, 0.057 mol, 1.1 eq) was added into the solution and stirred at −50° C. for about 1 hour. Upon completion, the mixture is warmed and heated to reflux for about 1 hr. After completion, water (115 mL) and ethyl acetate (40 mL×2) was added for extraction about two times. The combined organic layer was washed with saturated sodium chloride (80 mL) and concentrated to dryness to afford a crude oil. The oil was purification via column chromatography (EA (ethyl acetate)/n-heptane=3/7) to afford colorless oil (11.93 g) Yield: 78%. $^1$H NMR (400 MHz, CDCl$_3$) δ7.36 (m, 10H), 6.27 (d, 1H), 5.05 (d, 1H), 4.93 (m, 1H), 4.9-4.58 (m, 10H), 3.98 (m, 1H), 3.60 (m, 2H), 3.10 (m, 1H), 2.52 (m, 1H), 2.20 (m, 1H), 2.05 (m, 1H).

Example 9

Reaction 3b

Preparation of (1R,2R,3R,4S)-2-(hydroxymethyl)-4-(methoxymethoxy)-3-((methoxymethoxy)methyl)cyclopentanol (M4 with MOM protection)

To a flame-dried 500 mL three-necked flask was charged sequentially with NaHCO$_3$ (1.55 g, 18.4 mmol), anhydrous MeOH (36 mL), anhydrous CH$_2$Cl$_2$ (180 mL), and M3 (4.5 g, 18.4 mmol). The solution was cooled to −60 to −78° C. and treated with O$_3$ until a deep blue color developed and persisted (approximately 0.5 to 2 hr). The solution was subsequently flushed with O$_2$ for 10 to 15 min until the blue color is faded. Solid NaBH$_4$ (2.1 g, 55.2 mmol) was added portion-wise over a period of 10 min at −78° C. until complete disappearance of starting material was observed by TLC. The reaction mixture was warmed to 0° C. and stirred for about 1 hr. After stirring, the mixture was quenched by 1 N HCl aqueous solution, saturated NaCl aqueous solution and extracted with ethyl acetate for about two times. The organic layer was combined and concentrated to dryness to afford a crude oil. The oil is purification via column chromatography to afford colorless oil. Yield: 4.56 g (about 95%). $^1$H NMR (400 MHz, CDCl$_3$) δ4.50 (m, 4H), 4.40 (m, 1H), 4.10 (m, 3H), 3.63 (m, 2H), 3.40 (m, 6H), 2.32 (m, 1H), 2.13 (m, 1H), 2.10 (m, 2H); LRMS [MH$^+$] calcd for C$_{11}$H$_{22}$O$_6$ m/z 250.1. Found 250.1.

Example 10

Reaction 3b

Preparation of (1R,2R,3R,4S)-4-((benzyloxy)methoxy)-3-(((benzyloxy)methoxy)methyl)-2-(hydroxymethyl)cyclopentanol (M4 with BOM protection)

To a flame-dried 500 mL three-necked flask was charged sequentially with NaHCO$_3$ (2.53 g, 30.11 mmol, 1.0 eq), CH$_2$Cl$_2$ (240 mL), MeOH (48 mL), and M3 (11.93 g, 30.11 mmol, 1.0 eq). The solution was cooled to −60 to −78° C. and treated with O$_3$ gas until a light blue color developed and persisted (approximately 0.5 to 1 hr). The solution was subsequently flushed with O$_2$ for 10 to 15 min until the blue color is faded. Powder NaBH$_4$ (3.41 g, 90.33 mmol, 3 eq) was added portion-wise over a period of 10 min at −78° C. until completing disappearance of starting material was observed by TLC. The reaction mixture was warmed to 0° C. and stirred for about 2 hr. Then the mixture was quenched by saturated NaCl solution (30 mL), 0.5N HCl aqueous solution (30 mL), and extracted with CH$_2$Cl$_2$ (150 mL) for about two times. The organic layer was combined and concentrated to dryness to afford a crude oil. Yield: 12.6 g.

Module 1: elimination steps of M4 to M5

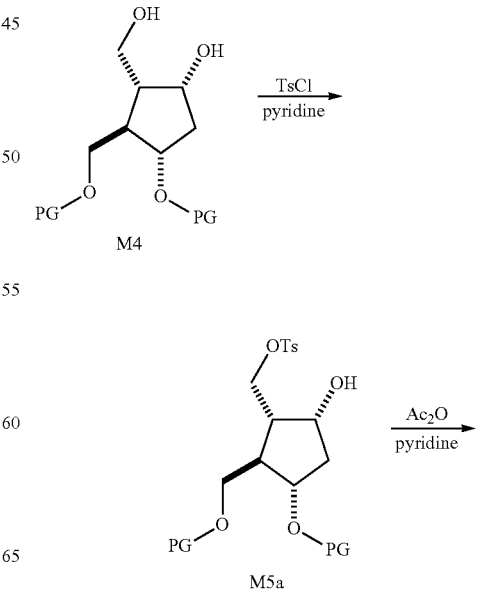

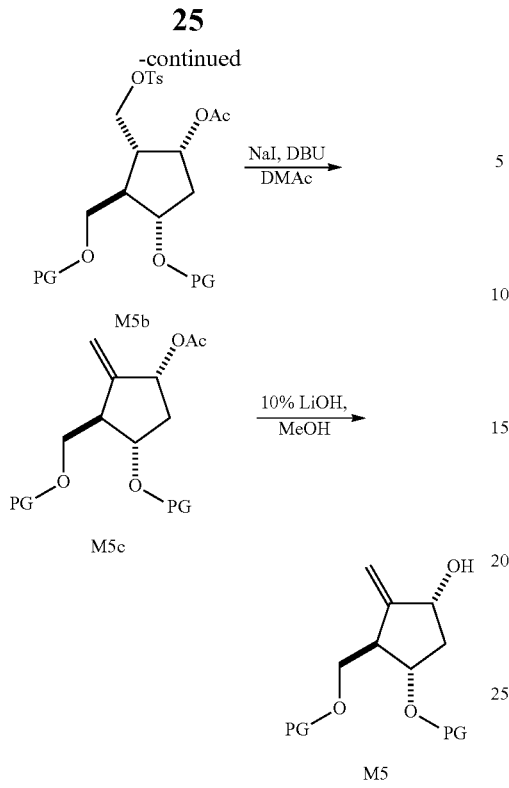

Example 11

Reaction 3c

Preparation of (((1R,2R,3S,5R)-5-hydroxy-3-(methoxymethoxy)-2-((methoxymethoxy)methyl)cyclopentyl)methyl 4-methylbenzenesulfonate (M5a with MOM protection)

To a stirred solution of M4 (600.0 mg, 2.4 mmol) and pyridine (246.8 mg, 3.12 mmol) in CH$_2$Cl$_2$ (60 mL) was stirred for 30 min at 10 to 0° C. Then p-TsCl (551.2 mg, 2.89 mmol) is added into the solution and warmed and stirred at room temperature for about 6 hr. After completion, 10% HCl aqueous solution was added to quench the reaction and CH$_2$Cl$_2$ was added for extraction about two times. The organic layer was combined and concentrated to dryness to afford a crude oil. The oil is purification via column chromatography to afford colorless oil. Yield: 450 mg (about 60%). $^1$H NMR (400 MHz, CDCl$_3$) δ7.78 (d, 2H), 7.32 (d, 2H), 4.59 (m, 4H), 4.32 (m, 1H), 4.22 (m, 2H), 4.06 (m, 1H), 3.54 (m, 2H), 3.33 (m, 6H), 2.43 (s, 3H), 2.02 (m, 3H); $^{13}$C NMR (100 MHz, CDCl$_3$) δ144.8 (C), 133.0 (C), 129.8 (2CH), 127.9 (2CH), 96.5 (CH$_2$), 95.1 (CH$_2$), 80.3 (CH), 73.2 (CH), 70.2 (CH$_2$), 68.2 (CH$_2$), 55.4 (CH$_3$), 55.3 (CH$_3$), 47.7 (CH), 46.7 (CH), 40.2 (CH$_2$), 22.7 (CH$_3$); LRMS [MH$^+$] calcd for C$_{18}$H$_{28}$O$_8$S m/z 404.15. Found 404.15.

Preparation of (((1R,2R,3S, 5R)-5-acetoxy-3-(methoxymethoxy)-2-((methoxymethoxy)methyl)cyclopentyl)methyl 4-methylbenzenesulfonate (M5b with MOM protection)

To a stirred solution of M5a (150.0 mg, 0.37 mmol) and pyridine (0.06 mL, 0.74 mmol) in CH$_2$Cl$_2$ (10 mL) was stirred for 30 min at 10 to 0° C. Then Ac$_2$O (0.07 mL, 0.74 mmol) is added into the solution and warmed and stirred at room temperature for about 6 hr. After completion, water was added to quench the reaction and CH$_2$Cl$_2$ was added for extraction about two times. The organic layer was combined and concentrated to dryness to afford a crude oil. The oil is purification via column chromatography to afford colorless oil. Yield: 100 mg (about 60%). $^1$H NMR (400 MHz, CDCl$_3$) δ7.78 (d, 2H), 7.35 (d, 2H), 5.14 (m, 1H), 4.59 (m, 4H), 4.24 (m, 2H), 4.00 (m, 1H), 3.58 (m, 2H), 3.34 (m, 6H), 2.47 (s, 3H), 2.24 (m, 3H), 2.11 (s, 3H), 1.89 (m, 1H); $^{13}$C NMR (100 MHz, CDCl$_3$) δ170.3 (C), 144.8 (C), 133.1 (C), 129.8 (2CH), 127.9 (2CH), 96.5 (CH$_2$), 95.9 (CH$_2$), 78.1 (CH), 74.0 (CH), 68.1 (CH$_2$), 66.9 (CH$_2$), 55.3 (2CH$_3$), 47.5 (CH), 43.4 (CH), 38.4 (CH$_2$), 21.6 (CH$_3$), 21.0 (CH$_3$); LRMS [MH$^+$] calcd for C$_{20}$H$_{30}$O$_9$S m/z 404.15. Found 446.16

Preparation of (1R,3R,4S)-4-(methoxymethoxy)-3-((methoxymethoxy)methyl)-2-methyl-enecyclopentyl acetate (M5c with MOM protection)

To a stirred solution of M5b (70.0 mg, 0.157 mmol), LiI (105.1 mg, 0.785 mmol) and DBU (239.0 mg, 1.57 mmol) in DMAc (4 mL) was stirred for 30 min at room temperature. Then, the resultant mixture is heated to 100° C. and stirred for about 2 hr. After completion, 10% HCl was added to quench the reaction and ethyl acetate was added for extraction about two times. The organic layer was combined and concentrated to dryness to afford a crude oil. The oil is purification via column chromatography to afford colorless oil. Yield: 50 mg (about 90%). $^1$H NMR (400 MHz, CDCl$_3$) δ5.50 (m, 1H), 5.28 (m, 2H), 4.69 (m, 4H), 4.64 (m, 2H), 4.05 (m, 1H), 3.64 (m, 2H), 3.38 (m, 6H), 2.89 (m, 1H), 2.58 (m, 1H), 2.11 (m, 3H), 1.80 (m, 1H).

Preparation of (1R,3R,4S)-4-(methoxymethoxy)-3-((methoxymethoxy)methyl)-2-methyl-enecyclopentanol (M5 with MOM protection)

10% LiOH aqueous solution (1.0 mL) was charged to a stirred solution of M5c (70.0 mg, 0.157 mmol) in MeOH (5 mL) and stirred for 30 min at room temperature. After completion, the solvent is removed by vacuum and 10% HCl was added to quench the reaction and ethyl acetate was added for extraction about two times. The organic layer was combined and concentrated to dryness to afford a crude oil. The oil is purification via column chromatography to afford colorless oil. Yield: 40 mg (about 94%).
$^1$H NMR (400 MHz, CDCl$_3$) δ5.38 (m, 1H), 5.20 (m, 1H), 5.28 (m, 2H), 4.69 (m, 4H), 4.64 (m, 2H), 4.45 (m, 1H), 4.15 (m, 1H), 3.60 (m, 2H), 3.58 (m, 6H), 2.94 (m, 1H), 2.28 (m, 1H+OH), 1.89 (m, 1H); LRMS [MH$^+$] calcd for C$_{11}$H$_{20}$O$_5$ m/z 232.13. Found 232.13

Example 12

Reaction 3c

Preparation of ((1R,2R,3S,5R)-3-((benzyloxy)methoxy)-2-(((benzyloxy)methoxy)methyl)-5-hydroxycyclopentyl)methyl 4-methylbenzenesulfonate (M5a with BOM protection)

To a stirred solution of p-toluenesulfonyl chloride (5.9 g, 2.89 mmol) and pyridine (33 mL) was stirred at 50° C. for 30 min. Then the solution was cooled to 0-10° C. M4 (8.23 g, 2.4 mmol) in CH$_2$Cl$_2$ (60 mL) was added into the solution at 0-10° C. and warmed to stir at room temperature for about 1 hour. After completion, 0.5N HCl (49 mL) was added to quench the reaction at 0-10° C. and CH₂Cl₂ (50 mL×2) was added for extraction about two times. The combined organic layer was washed with 10% citric acid (90 mL) and saturated sodium chloride (50 mL) separately. Then the organic layer was collected and dried over anhydrous magnesium sulfate. Evaporation of the solvent gave a crude oil. The of was purification via column chromatography (EA/n-heptane=3:7) to afford colorless oil of M5a (7.51 g) and recycled M4 (1.84 g). Yield: 66%

Preparation of ((1R,2R,3S,5R)-3-((benzyloxy)methoxy)-2-((benzyloxy)methoxy)methyl)-5-acetoxycyclopentyl)methyl 4-methylbenzenesulfonate (M5b with BOM protection)

To a stirred solution of M5a (7.36 g, 13.22 mmol) and 4-(dimethylamino)pyridine (9.69 g, 79.33 mmol, 6 eq) in CH₂Cl₂ (60 mL) was stirred for 30 min at 10 to 0° C. Then acetic anhydride (2.5 mL, 26.44 mmol, 2 eq) is added into the solution and warmed and stirred at r.t. for about 2 hr. After completion, water (25 mL) and 10% citric acid (30 mL) was added to quench the reaction separately and CH₂Cl₂ (50 mL) was added for extraction about two times. The combined organic layer was washed with saturated sodium chloride solution (50 mL). Then the organic layer was collected and dried over anhydrous magnesium sulfate. Evaporation of the solvent gave a crude oil (8.10 g).

Preparation of (1R,3R,4S)-4-((benzyloxy)methoxy)-3-(((benzyloxy)methoxy)methyl)-2-methylenecyclopentanol (M5 with BOM protection)

To a stirred solution of M5b (8.10 g), and Lithium iodide (8.85 g, 66.14 mmol, 5 eq) in DMAc (80 mL) was stirred for 30 min at r.t. Then, the resultant mixture is heated to 90 to 100° C. and stirred for about 1 hr. After completion, the mixture was cooled to r.t. and DBU (20.14 g, 132.29 mmol, 10 eq) was added and the resultant mixture is heated to 90 to 100° C. and stirred for about 16 hr. After completion, 10% HCl (42 mL) was added to quench the reaction and ethyl acetate (50 mL×3) was added for extraction about three times. The combined organic layer was washed with saturated sodium chloride solution (50 mL). Then the organic layer was collected and dried over anhydrous magnesium sulfate. Evaporation of the solvent gave a crude oil. The oil is purification via column chromatography (EA/n-heptane=3/7) to afford colorless oil (3.53 g). Yield: 69% over two steps. ¹H NMR (400 MHz, CDCl₃) δ7.39 (m, 10H), 5.40 (d, 1H), 5.21 (d, 1H), 4.8-4.57 (m, 8H), 4.45 (m, 1H), 4.26 (m, 1H), 3.67 (m, 2H), 2.98 (m, 1H), 2.47-1.98 (m, 3H).

Module 1: alternative elimination of steps M4 to M5

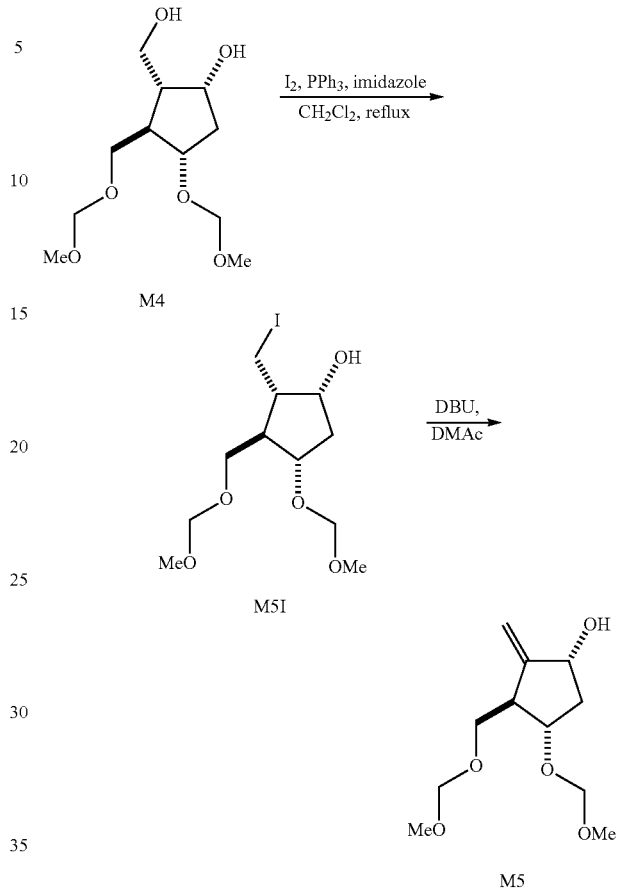

Example 13

Reaction 3c

Preparation of (1R,2S,3R,4S)-2-(iodomethyl)-4-(methoxymethoxy)-3-((methoxymethoxy)methyl)cyclopentanol (M5I with MOM Protection)

To a stirred solution of M4 (100.0 mg, 0.4 mmol), I₂ (253.8 mg, 1.0 mmol) and PPh₃ (262.3 mg, 1.0 mmol) in CH₂Cl₂ (10 mL) was stirred for 30 min at room temperature. Then, the resultant mixture is heated to reflux and stirred for about 2 hr. After completion, 10% HCl was added to quench the reaction and CH₂Cl₂ was added for extraction about two times. The organic layer was combined and concentrated to dryness to afford a crude oil. The oil is purification via column chromatography to afford colorless oil. Yield: 100 mg (about 70%). ¹H NMR (400 MHz, CDCl₃) δ4.64 (m, 4H), 4.30 (m, 1H), 4.20 (m, 1H), 3.60 (m, 2H), 3.40 (m, 8H), 2.38 (m, OH), 2.11 (m, 2H), 2.01 (m, 2H).

Preparation of (1R,3R,4S)-4-(methoxymethoxy)-3-((methoxymethoxy)methyl)-2-methyl-enecyclopentanol (M5 with MOM protection)

To a stirred solution of M5I (100.0 mg) and DBU (5 mL) in DMAc (5 mL) was stirred for 30 min at room temperature. Then, the resultant mixture is heated to 100° C. and stirred for about 2 hour. After completion, 10% HCl was added to quench the reaction and ethyl acetate was added for extraction about two times. The organic layer was combined and concentrated to dryness to afford a crude oil. The oil is purification via column chromatography to afford colorless oil. Yield: 50 mg (about 90%). $^1$H NMR (400 MHz, CDCl$_3$) δ 5.50 (m, 1H), 5.28 (m, 2H), 4.69 (m, 4H), 4.64 (m, 2H), 4.05 (m, 1H), 3.64 (m, 2H), 3.38 (m, 6H), 2.89 (m, 1H), 2.58 (m, 1H), 2.11 (m, 3H), 1.80 (m, 1H).

Module 2: oxidative cleavage steps

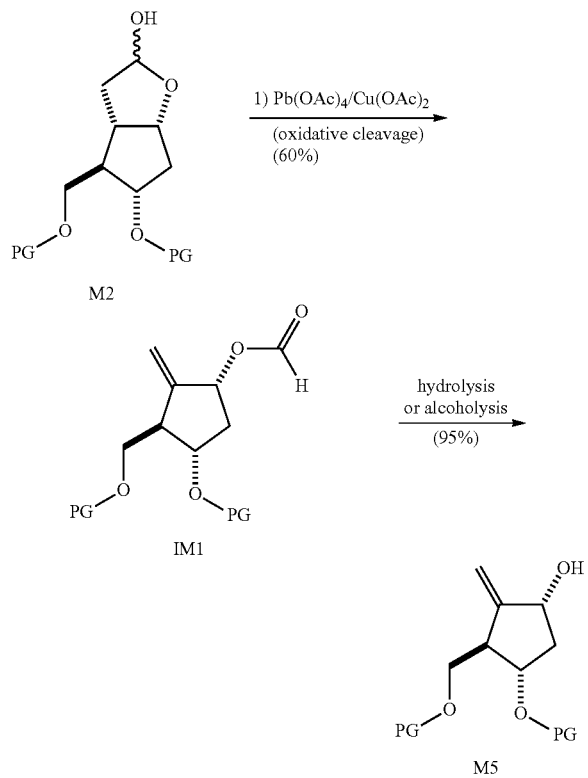

Example 14

Reaction 3d

A Preparation of (1R,3R,4S)-4-((benzyloxy)methoxy)-3-(((benzyloxy)methoxy)methyl)-2-methylenecyclopentanol (M5 with BOM protection)

To a stirred solution of M2 (0.5 g, 1.2 mmol), Pb(OAc)$_4$ (0.85 g, 1.92 mmol, 1.6 eq) or PhI(OAc)$_2$ (0.62 g, 1.92 mmol, 1.6 eq) and Cu(OAc)$_2$ (0.04 g, 0.216 mmol, 0.18 eq) in benzene or a suitable organic solvent (50 mL) was stirred at room temperature for about 4 hours and the resulted solution was heated to reflux. After 4 h for the completion, the mixture was cooled to room temperature and filtered through a pad of Celite®. After removing solvent by vacuum, the formate intermediate was formed as the green oil. $^1$H NMR (400 MHz, CDCl$_3$) δ 8.16 (s, 1H), 7.37 (m, 10H), 5.69 (m, 1H), 5.39 (d, 1H), 5.32 (d, 1H), 4.86-4.60 (m, 8H), 4.22 (m, 1H), 3.74 (m, 2H), 3.00 (m, 1H), 2.54 (m, 1H), 1.98 (m, 1H).

The crude oil is added into a solution contained 10% NaOH (3 mL) and methanol (10 mL) and stirred at room temperature for about 1 h. After the completion, 10% HCl was added to quench the reaction and ethyl acetate was added for extraction about two times. The organic layer was combined and concentrated to dryness to afford a crude oil. After isolation via column chromatography, the desired M5 is afforded colorless oil 125 mg. Yield: 30~60% over two steps.

Example 15

Reaction 3d

A Preparation of IM1 with Ethylidene Protection

Charge M2 (, 0.931 kg, 1.0 eq), Cu(OAc)$_2$ (0.149 kg, 0.18 eq), pyridine (0.121 kg, 0.3 eq), and 1,2-dichloroethane (13.74 kg) into a suitable vessel under nitrogen. And the resulting mixture was heated to 50 to 80° C. and then Pb(OAc)$_4$ (3.286 kg, 1.6 eq) was charged into the mixture. After addition is complete, the reaction mixture is stirred for about 1 h at 50 to 80° C.

The following work procedures could be:

(A) The mixture was then cooled to room temperature and filtered through a pad of Celite® and washed with dichloromethane (3.70 kg). The filtrate is collected and water (4.66 kg) is added to reaction mixture at 20 to 35° C. and settles for phase separation. After phase separation, the organic phase is collected and the aqueous layer is continued to extract with dichloromethane (3.70 kg). After phase separation, the organic layer is collected and combined the dichloromethane layer with the previous organic layer and then performing distillation until 2 v/w (based on M2), the crude IM1 solution was obtained as the brown or green oil. This crude oil was purified by column chromatography to afford white solid (350 g). Yield: 40-60%. $^1$H NMR (400 MHz, CDCl$_3$) δ 8.07 (s, 1H), 5.54 (m, 1H), 5.26 (d, 1H), 4.94 (d, 1H), 4.70 (m, 1H), 4.40 (m, 1H), 3.65 (m, 1H), 3.29 (m, 1H), 2.70-2.53 (m, 2H), 1.82 (m, 1H), 1.36 (m, 3H).

(B) The mixture is added into n-heptane and then heated to 50-70° C., and then filtered through a pad of silica gel. The filtrate is collected and subsequently the solution is performed to distill until slurry. Filter the solid and dry under vacuum to afford IM1 as a white solid. Yield: 60-65%.

Example 16

Reaction 3d

A Preparation of M5 with Ethylidene Protection

Charge IM1 (0.33 kg, 1.66 mol, 1.0 eq) and methanol (2.6 L) into a suitable vessel under nitrogen. Then triethylamine (0.087-0.097 kg, 0.83-1.00 mol, 0.5 eq-0.6 eq) was added into the solution at 20 to 35° C. for about 1 h. The resultant mixture was stirred at room temperature for about 1 hr. After completion, the resultant solution is reduced volume and replaced via solvent swap with MTBE (0.66 L). The reaction mixture is filtered through a pad of silica gel. Subsequently the filtrate is collected and washed with MTBE (1.32 L). The resultant solution is reduced volume by distillation until 1 L and then n-heptane (9.3 L) was charged into the mixture at below 50° C. The mixture is cooled to about 50° C. and seeded until cloud point is observed. The mixture is cooled to −10 to 0° C. The solid is filtered and washed with n-heptane. The wet cake is dried at NMT 30° C. under vacuum to afford M5 (PG=ethylidene, about 325 g). Yield: 85-95%. $^1$H NMR (400 MHz, CDCl$_3$) δ 5.12 (d, 1H), 4.81 (d, 1H), 4.64 (m, 1H), 4.38-4.30 (m, 2H), 3.56 (m, 1H), 3.17 (m, 1H), 2.53 (m, 3H), 1.62 (m, 1H), 1.30 (m, 3H).

Synthesis of N2-Boc-2-amino-6-iodopurine

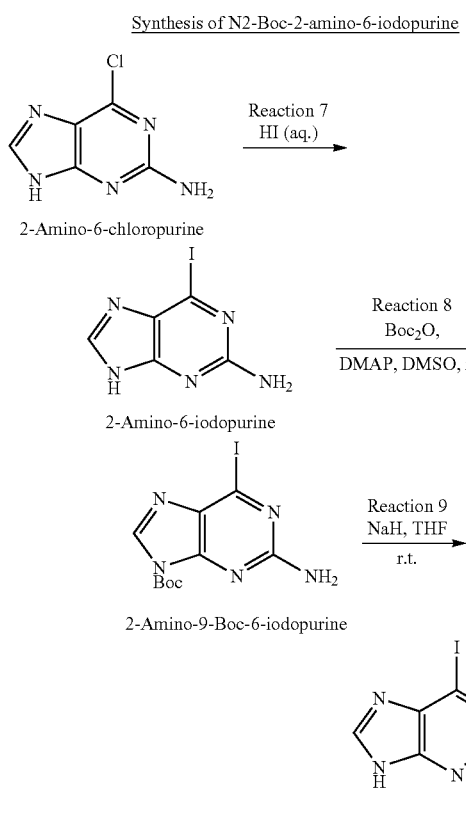

Example 17

Reaction 7

Preparation of 2-amino-6-iodopurine

Charge 57% Hydriodic acid (10.90 kg) into a suitable vessel under nitrogen and then the solution was cooled to 0 to 10° C. Then 2-amino-6-chloropurine (0.8 kg) was charged into the solution at about 15° C. After 2 h for the completion, water (8 kg) was slowly charged to the reaction mixture at r.t. and stirred for about 0.5 h. The yellow precipitate was filtered and washed with water. The wet cake was transferred to a suitable vessel, and water (2.0 kg) and 20% NaOH aqueous solution (0.4 kg) were slowly charged to dissolve the solids at r.t. Then THF (2.14 kg) was charged into the solution and 10% HOAc (4.8 kg) was slowly charged into the solution at about 35° C. to observe slurry mixture. The resultant slurry was stirred filtered and washed with acetone (3.8). The wet cake was dried under vacuum at 70° C. to afford SPT1255C1 (1.14 kg). Yield: 90-98%. $^1$H NMR (400 MHz, DMSO-d6) 6.65 (s, 2H, NH$_2$), 8.04 (s, 1H, H$_8$)

Example 18

Reaction 8

Preparation of 2-amino-9-Boc-6-iodopurine

Charge 2-amino-6-iodopurine (9.528 kg, 1 eg), 4-Dimethylaminopyridine (0.22 kg) and DMSO (106.05 kg) into a suitable vessel under nitrogen and then the solution was stirred at room temperature. Then Di-tert-butyl dicarbonate (8.75 kg, 1.1 eq) was slowly charged at r.t. and the resultant solution was stirred at r.t. After 1 h for the completion, water (47.7 kg) was charged to the reaction mixture to quench the reaction and DCM (163.9 kg) was charged for phase separation. The organic layer was collected and dried to afford crude 2-amino-9-Boc-6-iodopurine solution for the next step using. $^1$H NMR (400 MHz, DMSO-d6) 8.38 (s, 1H), 7.18 (s, 2H, NH$_2$), 1.60 (s, 9H).

Example 19

Reaction 9

Preparation of N2-Boc-2-amino-6-iodopurine

Charge 2-amino-9-Boc-6-iodopurine solution into a suitable vessel under nitrogen and the solution were cooled to 0 to 10° C. Then 60% sodium hydride (4.7 kg, about 3.0 eq) was portion-wise charged into the solution at 0 to 15° C. After 2 h for the completion, 20% brine (28.6 kg) was slowly charged into the solution. After phase separation, the organic layer was washed with of 10% NaOH (19.1 kg) and 20% brine (19.1 kg). Then the organic layer is collected and 10% HOAc (21 kg) was charged to the solution. After phase separation, the organic layer was collected and fresh filtered with a pad of silical gel and the filtrate was collected and distillation at about 60° C. until observing a yellow slurry solution (the volume is about 8 v/w). Subsequently, n-heptane (39.1 kg) was charged into the mixture and cool down to −5 to 10° C. for about 1 hr. The slurry solution was filtered and washed with n-heptane (13.15 kg). The wet cake was dried under vacuum at 70° C. to afford N2-Boc-2-amino-6-iodopurine (9.662 kg, 75-85% over two steps). $^1$H NMR (400 MHz, d$_6$-DMSO) δ 1.46 (s, 9H, 3CH$_3$), 8.42 (s, 1H, H$_8$), 10.15 (s, 1H, NH)

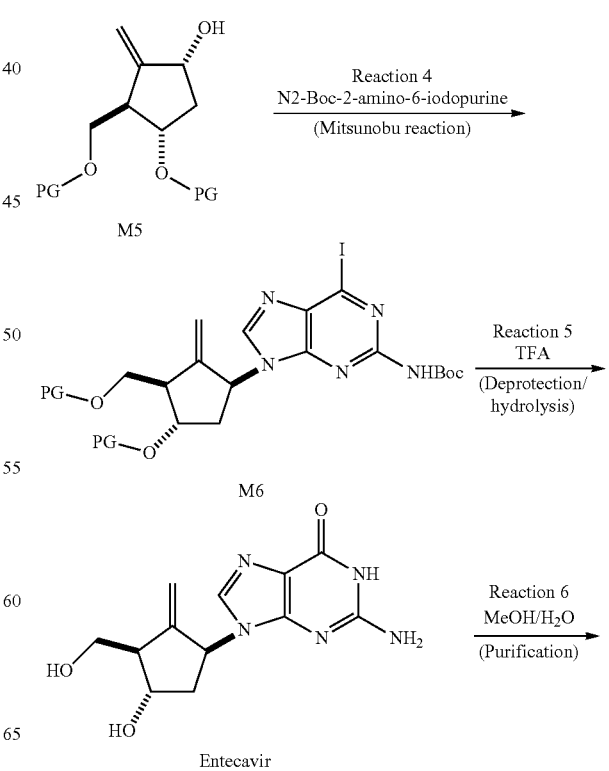

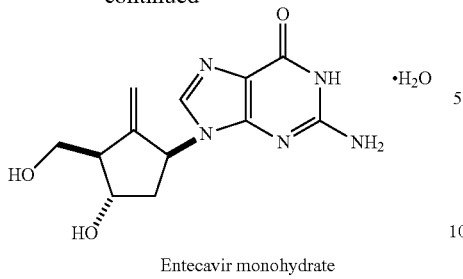

Entecavir monohydrate

Example 20

Reaction 4

Preparation of tert-butyl 6-iodo-9-((1S,3R,4S)-4-(methoxymethoxy)-3-((methoxymethoxy)methyl)-2-methylenecyclopentyl)-9H-purin-2-ylcarbamate (M6 with MOM protection)

To a stirred solution of M5 (100.0 mg, 0.43 mmol), PPh$_3$ (225.6 mg, 0.8.6 mmol) and N2-Boc-2-amino-6-iodopurine (310.6 mg, 0.86 mmol) in THF (5 mL) was stirred for 30 min at 0° C. Then, DEAD (150.0 mg, 0.86 mmol) is slowly charged into the solution at about 0° C. The resultant mixture is warmed to room temperature and stirred for about 2 h. After completion, the solution is concentrated to dryness to afford a crude oil. The oil is purification via column chromatography to afford colorless oil. Yield: 123 mg (about 60%).

$^1$H NMR (400 MHz, CDCl$_3$) δ8.15 (s, 1H), 7.63 (s, NH), 5.64 (m, 1H), 5.32 (d, 1H), 4.94 (d, 1H), 4.70 (m, 2H), 4.36 (m, 1H), 3.85 (m, 2H), 3.39 (s, 3H), 3.37 (s, 3H), 2.93 (m, 1H), 2.47 (m, 2H), 1.55 (s, 9H); LRMS [MH$^+$] calcd for C$_{21}$H$_{30}$IN$_5$O$_6$ m/z 575.12. Found 575.12

Example 21

Preparation of Entecavir

To a stirred solution of M6 (PG=MOM, 100.0 mg, 0.173 mL) and 10% NaOH (excess) in Dioxane/THF (1:9, 5 mL) was stirred for about 12 hr at 50-60° C. After completion, saturated NH$_4$Cl was added to quench the reaction and ethyl acetate was added for extraction about two times. The organic layer was combined and concentrated to dryness to afford a crude solid. The solid is purification via column chromatography to afford colorless solid. Yield: 50 mg (about 80%). $^1$H NMR (400 MHz, DMSO-d6) δ10.72 (s, 1H), 7.67 (s, 1H), 6.57 (s, 2H), 5.32 (m, 1H), 5.17 (d, 1H), 4.65 (m, 5H), 4.20 (m, 1H), 3.64 (m, 2H), 3.27 (s, 3H), 3.26 (s, 3H), 2.84 (m, 1H), 2.35 (m, 2H). And then the solid was added into aqueous 10% HCl solution in DMSO/THF (1:9, 5 mL) was stirred for 2 h at 50-60° C. After completion, the solution is concentrated to dryness to afford a crude solid. The solid is purification via column chromatography to afford white solid. Yield: about 85% for the entecavir salt form. $^1$H NMR (400 MHz, DMSO-d6) δ11.62 (s, 1H), 8.68 (s, 1H), 7.32 (s, 2H), 5.44 (m, 1H), 5.18 (d, 1H), 4.75 (s, 1H), 4.18 (m, 1H), 3.64 (m, 2H), 3.10 (m, 1H), 2.15 (m, 2H). Then The salt form will be neutralized by base (K$_2$CO$_3$) to give the corresponding free form of entecavir as white solid. Yield: about 95%. $^1$H NMR (400 MHz, DMSO-d6) δ10.4 (s, 1H), 7.65 (s, 1H), 6.73 (s, 2H), 5.35 (m, 1H), 5.10 (d, 1H), 4.95 (s, 1H), 4.90 (t, 1H), 4.56 (s, 1H), 4.20 (m, 1H), 3.53 (m, 2H), 3.13 (m, 1H), 2.23 (m, 1H), 2.05 (m, 1H).

Example 22

Reaction 5

Preparation of Entecavir

To a stirred solution of M6 (PG=MOM, 30.0 mg) and 80% TFA (5 mL) was stirred for 2 h at 50-60° C. After completion, the solution is neutralization by aqueous NH$_4$OH solution and then concentrated to dryness to afford a crude solid. The solid is recrystallization by water and methanol to afford white solid. Yield: about 85%. $^1$H NMR (400 MHz, DMSO-d6) δ10.4 (s, 1H), 7.65 (s, 1H), 6.73 (s, 2H), 5.35 (m, 1H), 5.10 (d, 1H), 4.95 (s, 1H), 4.90 (t, 1H), 4.56 (s, 1H), 4.20 (m, 1H), 3.53 (m, 2H), 3.13 (m, 1H), 2.23 (m, 1H), 2.05 (m, 1H).

Example 23

Reaction 4

Preparation of Tert-Butyl 9-((1S,3R,4S)-4-((benzyloxy)methoxy)-3-(((benzyloxy)methoxy)methyl)-2-methylenecyclopentyl)-6-iodo-9H-purin-2-ylcarbamate (M6 with BOM protection)

To a stirred solution of M5 (0.768 g, 2.0 mmol, 1 eq)), PPh$_3$ (1.05 g, 4.0 mmol, 2 eq) and N2-Boc-6-iodopurine (1.45 g, 4.0 mmol, 2 eq) in THF (5 mL) was stirred for 30 min at 0° C. Then, DEAD (0.7 g, 4.0 mmol, 2 eq) is slowly charged into the solution at about 0° C. The resultant mixture is warmed to r.t. and stirred for about 2 hour. After completion, the solution is concentrated to dryness to afford a crude oil. The oil is purification via column chromatography (EA/n-heptane=317) to afford colorless oil (1.1 g). Yield: 70%.

Example 24

Reaction 5: Preparation of Entecavir

Method A: To a stirred solution of M6 (PG=BOM, 200.0 mg, 0.173 mL) and 10% NaOH (excess) in dioxane/THF (1:9, 5 mL) was stirred for about 12 hr at 50-70° C. After completion, saturated NH$_4$Cl was added to quench the reaction and ethyl acetate was added for extraction about two times. The organic layer was combined and concentrated to dryness to afford a crude solid. The solid is purification via column chromatography to afford colorless solid. Yield: 50 mg (about 40%). $^1$H NMR (400 MHz, DMSO-d6) δ10.72 (s, 1H), 7.69 (s, 1H), 7.29 (m, 10H), 6.47 (s, 2H), 5.35 (m, 1H), 5.17 (d, 1H), 4.73 (m, 4H), 4.62 (m, 1H), 4.54 (m, 4H), 4.30 (m, 1H), 3.70 (m, 2H), 2.88 (m, 1H), 2.37 (m, 1H), 2.27 (m, 1H); $^1$H NMR (100 MHz, DMSO-d6) δ 157.3 (C), 154.1 (C), 151.9 (C), 150.3 (C), 138.5 (2C), 136.2 (CH), 128.7 (2CH), 128.2 (2CH), 128.1 (2CH), 128.0 (2CH), 127.9 (2CH), 116.8 (C), 110.3 (CH$_2$), 94.8 (CH$_2$), 93.0 (CH$_2$), 76.7 (CH), 69.4 (2CH$_2$), 69.2 (CH$_2$), 55.6 (CH), 49.4 (CH), 36.6 (CH$_2$).

The solid and 10% HCl in DMSO/THF (1:9, 5 mL) were stirred for 2 hr at 50-60° C. After completion, the solution is quenched by sat. NaHCO$_3$ until pH is 6-8. Then the solution is concentrated to dryness to afford a crude solid. The solid is purification via column chromatography to afford white solid. Yield: about 81% for the entecavir. $^1$H NMR (400 MHz, DMSO-d6) δ 10.9 (s, 1H), 7.64 (s, 1H), 6.8 (s, 2H), 5.35 (t, 1H), 5.10 (s, 1H), 4.95 (s, 1H), 4.92 (t, 1H), 4.56 (s, 1H), 4.20

(s, 1H), 3.53 (t, 2H), 2.54 (m, 1H), 2.23 (m, 1H), 2.05 (m, 1H); $^{13}$C NMR (100 MHz, DMSO-d6) δ 157.33 (C), 153.79 (C), 151.93 (C), 151.65 (C), 136.55 (CH), 116.64 (C), 119.82 (CH$_2$), 70.85 (CH), 63.34 (CH$_2$), 55.63 (CH), 54.39 (CH), 40.4 (CH$_2$).

Method B: To a stirred solution of M6 (PG=BOM, 200.0 mg, 0.173 mL) and 80% TFA (5 mL) was stirred for 2 h at 50-80° C. After completion, the solution is neutralization by aqueous NH$_4$OH solution and then concentrated to dryness to afford a crude solid. The solid is recrystallization by water and methanol to afford white solid. Yield: about 85%.

Example 25

Reaction 4

A Preparation of M6 with Ethylidene

Charge M5 (80 g, 0.47 mol, 1.0 eq), N2-Boc-2-amino-6-iodopurine (220.7 g, 0.60 mol, 1.3 eq), PPh$_3$ (185 g, 1.5 eq) and dichloromethane (1040 mL) into a suitable vessel under nitrogen and then the solution was cooled down at −5 to 15° C. Diisopropyl azodicarboxylate (123.6 g, 1.3 eq) in dichloromethane (160 mL) was slowly charged at below 15° C. and the resultant solution was stirred at room temperature for about 3 h. 2% NaOH aqueous solution (800 mL) was charged to the reaction mixture to quench the reaction. After phase separation, the organic layer was collected and washed with water (800 mL). After phase separation, the organic layer was collected and then added portions MeOH (1600 mL) to execute distillation until cloudy. Subsequently, the slurry mixture was cooled down to 20 to 35° C. and hold for about 1 hr. The mixture was filtered and washed with MeOH (240 mL). The wet cake was dried under vacuum at 60° C. to afford M6 (170 g, 70%) and the purity is more than 99%. $^1$H NMR (400 MHz, CDCl$_3$) 7.94 (s, 1H, H-8), 7.52 (s, 1H, NH), 5.50 (d, 1H, CH), 5.03 (q, 1H, CH), 4.89 (s, 1H, CH$_2$), 4.61 (m, 2H, CH$_2$, CH$_2$), 4.47 (m, 1H, CH), 3.96 (t, 1H, CH$_2$), 2.47 (m, 2H, CH$_2$), 2.36 (m, 1H, CH), 1.55 (s, 9H), 1.44 (d, 3H, CH$_3$)

Example 26

Reaction 5: Preparation of Entecavir

Charge 80% trifluoroacetic acid aqueous solution (553 mL) into a suitable vessel and then the solution was heated to 70 to 85° C. The slurry solution of M6 (55.3 g) in THF (138 mL) was charged into above solution at 70 to 85° C. and rinse with THF (28 mL). The mixture was stirred at 70 to 85° C. for about 1.5 h. After completion, water (400 mL) was charged into the solution and the solvent was reduced by distillation until volume was reaching about 550 mL. Subsequently, dichloromethane (166 mL) was added and settle for the phase separation. The aqueous layer was collected and dichloromethane (166 mL) was added for washing again and settle for the phase separation. The aqueous layer was collected and about 30% NH$_4$OH aqueous solution (55.3 mL) was added to adjust pH. Then, methanol (55 mL 1 v/w) was added to the mixture and the resultant mixture was heat to re-dissolve and then cooled to 10 to 30° C. The slurry was filtered and washed with of water (55 mL) to give about 32.1 g wet cake. Yield: 80-90%.

Example 27

Reaction 6: Preparation of Entecavir Monohydrate

To a stirred solution of M6 (32.1 g), water (240 mL) and methanol (144 mL) was stirred at 70 to 80° C. After dissolution, activated carbon (0.48 g) was added for de-coloration. The mixture was filtered through a pad of Celite® and rinsed with water (144 mL). It was cooled and seeded, after hold at cloud point for about 2 hr. The slurry was stirred at 10 to 30° C. for about 1 h. Then the mixture was filtered and washed with methanol (48 mL). The solids were dried at NMT 50° C. to afford entecavir monohydrate (22.5 g). Yield: 85-95%. EE: >99.5%, water content: 5-7%, all individual impurities are less than 0.10%, purity is more than 99.5%.

Example 28

Reaction 1: Preparation of M1 with p-Methoxyphenyldiphenylmethyl (MMTr) and TBS Protection Charge (+)-corey diol (5 g, 1.0 eq), of p-Methoxyphenyldiphenylmethyl chloride (MMTrCl) (9 g, 1.0 eq), Et$_3$N (10 mL, 2.5 eq), DMAP (0.18 g, 0.05 eq) and DCM (150 mL) into a suitable vessel under nitrogen and the mixture was stirred at below 35° C. for about 1 h. Then charge TBSCl (10.11 g, 1.2 eq) and DMF (50 mL) into the reaction mixture under nitrogen and stirred for about 24 h.

After completion, about 20% brine (200 mL) and DCM (200 mL) was added into the reaction mixture at below 35° C. and settle for phase separation. After phase separation, the organic phase is collected. Then reduce the solvent by distillation and perform solvent swap with toluene until cloudy. Subsequently, n-heptane is charged at about 40° C. The resultant slurry is cooling to −5 to 10° C. and stirred for about 1 h. The solids were filtered, washed with a cold (−5 to 10° C.) toluene. The wet cake was dried under vacuum at 60° C. to afford crystalline M1 (14.2 g). $^1$H NMR (400 MHz, CDCl$_3$) δ 7.4-6.8 (m, 14H), 4.91 (m, 1H), 4.14 (m, 1H), 3.82 (s, 3H), 3.06 (m, 2H), 2.76 (m, 1H), 2.60 (m, 2H), 2.10 (m, 2H), 1.92 (m, 1H), 0.89 (s, 9H), 0.09 (s, 3H), 0.05 (s, 3H).

Example 29

Reaction 2: Preparation of M2 with p-Methoxyphenyldiphenylmethyl (MMTr) and TBS Protection Charge M1 (7.2 g, 1.0 eq) and toluene (120 mL) into a suitable vessel under nitrogen and the solution is cooled to below −45° C. Then, DIBAL solution (19.3 mL, 1.0 M in toluene, about 1.5-1.6 eq) was charged into the solution at below −45° C. for about 0.5 h. After completion, the reaction is quenched by addition of methanol and then stirred at below −45° C. for about 0.5 h. Subsequently, water was added drop-wise at below 35° C. and the mixture was stirred for about 5 h. The solid was filtered and washed with MeOH and toluene. The filtrate was collected and reduced solvent by distillation at until the suitable volume. Subsequently, the mixture is seeded with M2 seed until cloud point is observed. The mixture is cooled to −5 to 10° C., and the solid is filtered and washed with cold n-heptane. The wet cake is dried at below 60° C. under vacuum to afford M2 (about 7.3 g). $^1$H NMR (400 MHz, CDCl$_3$) δ $^1$H NMR (400 MHz, CDCl$_3$) δ 7.4-6.8 (m, 28H), 5.68 (m, 1H), 5.30 (m, 1H), 5.28 (m, 1H), 4.62 (m, 1H), 4.18 (m, 1H), 3.82 (s, 6H), 3.18-3.0 (m, 4H), 2.76-2.0 (m, 13H), 0.89 (s, 9H), 0.78 (s, 9H), 0.07 (s, 6H), −0.03 (s, 6H).

Example 30

Reaction 3d: Preparation of IM1 with p-Methoxyphenyldiphenylmethyl (MMTr) and TBS Protection Charge M2 (7.3 g, 1.0 eq), Cu(OAc)$_2$ (0.42 g, 0.18 eq), pyridine (1.23 g, 0.3 eq), and 1,2-dichloroethane (10 mL) into a suitable vessel under nitrogen. And the resulting mixture was heated to 50 to 80° C. and then Pb(OAc)$_4$ (9.27 g, 1.6 eq) was charged into the mixture. After addition is complete, the reaction mixture is stirred for about 1 h at 50 to 80° C. The work up procedure is same as the above. Provide IM1 (~2.1 g). $^1$H NMR (400 MHz, CDCl$_3$) δ 7.3-6.8 (m, 14H), 5.27 (d, 1H), 4.99 (m, 1H), 4.27 (m, 2H), 3.7 (s, 3H), 3.05-2.80 (m, 3H), 1.8-1.6 (m, 2H), 0.9 (s, 9H), 0.016-0.009 (m, 6H).

The above-presented preferred embodiments may be modified in various ways in accordance with the spirit and principle of the present invention. For example, In Reaction 1 (protection) of the above shown SPT Scheme 1, the two diol protecting groups may be independently selected from the group consisting of cyclic ketals, acetal silanes, and acyclic protecting groups (such as benzyl, benzoyl, TBS, and TMS). Other potential useful protecting groups to protect the diol system can be found in Greene's Handbook "*Protective Groups in Organic Synthesis*".

In Reaction 2 (reduction) of the above shown SPT Scheme 1 the reducing agents may be selected from hydride reagents with lactone reducing ability.

In Reaction 3, Module 1 of the above shown SPT Scheme 1 ((Hydrolysis or alcoholysis), the hydrolysis of the formate ester intermediate could be replaced with other effective de-protection reactions, including hydride reduction or nucleophilic cleavage using nitrogen compounds, ammonia, organo-metallic reagents, and sulfides. The preferred reagents are Et$_3$N/MeOH and NaHCO$_3$/MeOH.

In Reaction 3, Module 2 of the above shown SPT Scheme I (oxidative cleavage), the oxidative cleavage may effected using Pb(OAc)$_4$/Cu(OAc)$_2$, PhI(OAc)$_2$/Cu(OAc)$_2$, I$_2$/AIBN, PbI(OAc)$_2$/I$_2$/AIBN, Mn(OAc)$_3$, CAN, Fe(OAc)$_3$, PhI(OAc)$_2$, Dess-Martin, IBX, etc. Meanwhile, Cu(OAc)$_2$ may be replaced with CuCl$_2$, CuBr$_2$, CuI$_2$, CuSO$_4$. Pyridine may be replaced with other bases, such as triethyl amine, 2-methylpyridine, DBU, diisopropylethyl amine, Na$_2$CO$_3$ and NaHCO$_3$. In addition to 1,2-dichloroethane used above, other organic solvents, such as benzene, toluene, anisole, chlorobenzene, xylene, ACN, THF, DME, DCM, pyridine, acetic acid, and cyclohexane, may be used in this reaction.

In Reaction 4 of the above shown SPT Scheme 1 (Mitsunobu reaction), DIAD may be replaced with other reagents, such as DEAD. PPh$_3$ may be replaced with other tri-substituted phosphines, such as diphenyl-2-pyridylphosphine, 4-(dimethylamino)phenyldiphenylphosphine, trialkyl phosphine (triethyl phosphine, tributylphosphine), triarylphosphine (trimethoxyphenyl phosphine, and trinitrophenyl phosphine. The preferred solvent is dichloromethane but other organic solvents may be used. The preferred purification solvent is an alcohol.

In Reaction 5 of the above shown SPT Scheme 1 (Hydrolysis/Deprotection), trifluoroacetic acid (TFA) may be replaced by other organic acids or inorganic acids. The solvent may be selected from the group consisting of THF, 2-methylTHF, acetone, ACN, C$_1$-C$_8$ alcohols, DMSO, DMAc, DMF, water, DCM, EA, n-heptane, MTBE, MIBK, and combinations thereof. The preferred acid is 80% TFA aqueous solution.

In Reaction 6 of the above shown SPT Scheme 1 (Purification), a solvent selected from the group consisting of EA, n-heptane, acetone, toluene, DCM, demineralized water, MTBE, DIPE, C$_1$-C$_8$ alcohols, DMSO, DMAc, DM, and combinations thereof may be used to crystallize the entecavir monohydrate.

The invention is not limited by the embodiments described above which are presented as examples only but can be modified in various ways within the scope of protection defined by the appended patent claims.

We claim:

1. A process of making entecavir of the following formula:

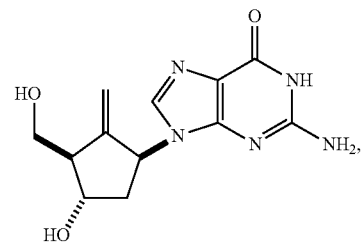 [SMILES: C=C1[C@H](CO)[C@@H](O)C[C@@H]1n1cnc2c(=O)[nH]c(N)nc21]

comprising reacting a compound of formula (M5)

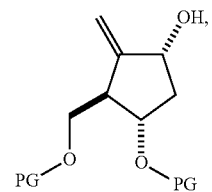

with a compound of formula (A):

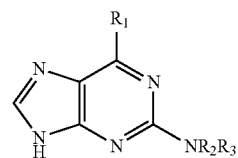

to give a compound of formula (M6):

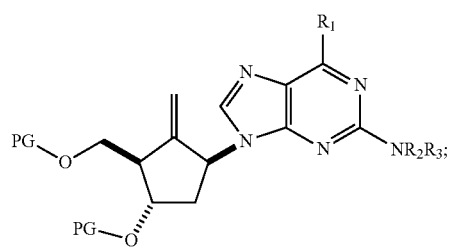

and de-protecting and/or hydrolyzing the compound of formula (M6) to obtain entecavir, wherein the two PGs on the formula (M5) are taken together with the two oxygen atoms to which they attach and the carbon atoms between the two oxygen atoms to form an optionally substituted six- or seven-member ring, R$_1$ on formulae (A) and M6 is halogen; R$_2$ and R$_3$ on formulae (A) and M6 are independently defined as H or an amino protecting group.

2. The process of claim 1 wherein the compound of formula M5 is a compound with one of the following formulae:

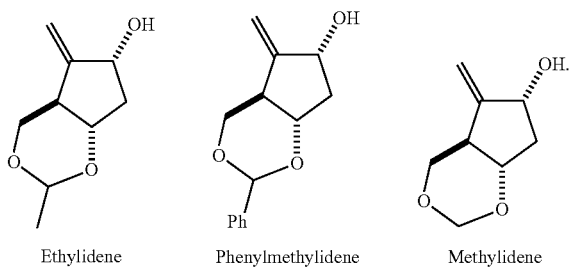

Ethylidene   Phenylmethylidene   Methylidene

3. The process of claim 1 wherein the compound of formula M5 is a compound of the following formula:

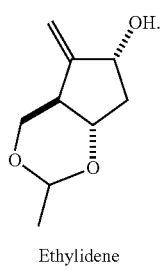

Ethylidene

4. The process of claim 1 wherein the reaction of the compound of formula (M5) and the compound of formula (A) to make the compound of formula (M6) is a Mitsunobu reaction carried out in the presence of a reagent selected from the group consisting of diethyl azodicarboxylate (DEAD), diisopropyl azodicarboxylate (DIAD), and combination thereof, a trisubstituted phosphine, and an organic solvent.

5. The process of claim 4 further comprising a step of isolating the compound of formula (M6) from a mixture formed from the reaction of the compound of formula (M5) and the compound of formula (A) by crystallization.

6. The process of claim 1 wherein on formulae A and M6, at least one of $R_2$ and $R_3$ is not H, and the process further comprises:

reacting a 6-substituted purine compound of formula

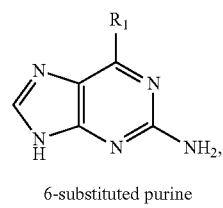

6-substituted purine wherein $R_1$ is as defined above in connection with the compound of formula (A), with an amino protecting reagent in an organic solvent at a temperature of from −60° C. to about reflux to yield the compound of formula (A).

7. The process of claim 1 further comprising steps of:
reducing a compound of formula (M1):

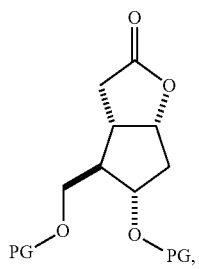

to give a compound of formula (M2):

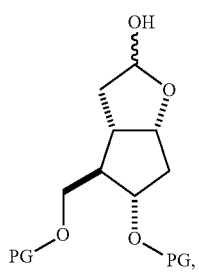

oxidizing the compound of formula (M2) to obtain a compound of formula (IM1)

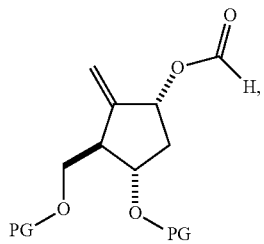

wherein the two PGs on each of the formulae (M1, M2, and IM1) are taken together with the two oxygen atoms to which they attach and the carbon atoms between the two oxygen atoms to form an optionally substituted six- or seven-member ring; and subjecting the compound of formula (IM1) to hydrolysis or alcoholysis so that it converts to the compound of formula (M5).

8. The process of claim 7 further comprising a step of isolating the compound of formula (M5) from a mixture resulted from the converting subjecting step by crystallization.

9. The process of claim 1 further comprising steps of:

reducing a compound of formula (M1):

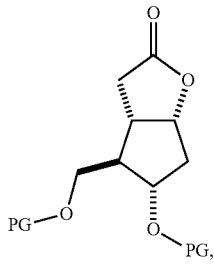
M1 to give a compound of formula (M2):

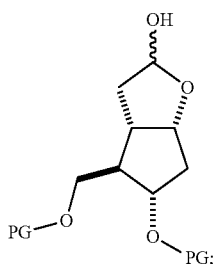
M2 dehydrating the compound of formula (M2) to provide a compound of formula (M3);

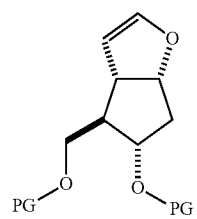
M3 oxidizing the compound of formula (M3) to obtain a compound of formula (M3IM)

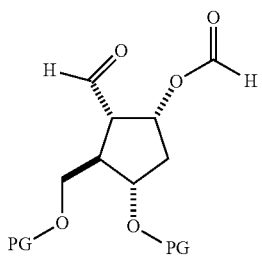
M3IM and reducing the compound of formula M3IM obtained from the oxidizing step to provide a compound of formula (M4)

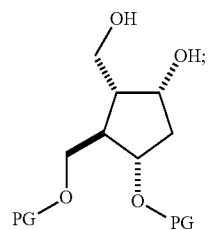
M4 and deyhydrating the compound of formula (M4) to the compound of formula (M5);

wherein the two PGs on each of the formulae (M1, M2, M3, M3IM, and M4) are taken together with the two oxygen atoms to which they attach and the carbon atoms between the two oxygen atoms to form an optionally substituted six- or seven-member ring.

10. The process of claim 9 wherein the step of dehydrating the compound of formula (M4) to the compound of formula (M5) comprises:

converting the compound of formula (M4) to give a protected compound of formula (M5b):

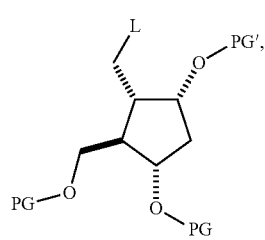
M5b wherein L is a leaving group, and PG' is acetyl;

removing the leaving group of the protected compound of formula (M5b) to give a compound of formula (M5c):

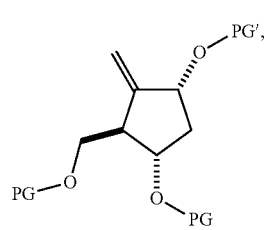
M5c wherein PG' is defined as above in connection with the formula M5b; and de-protecting the compound of formula (M5c) to obtain the compound of formula (M5);

wherein the two PGs on each the formulae (M5b) and (M5c) are taken together with the two oxygen atoms to which they attach and the carbon atoms between the two oxygen atoms to form an optionally substituted six- or seven-member ring.

11. The process of claim 7 further comprising converting (+)-Corey diol of formula

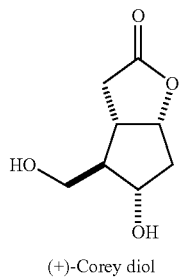
(+)-Corey diol to the compound of formula (M1).

12. The process of claim 11 further comprising a step of isolating the compound of formula (M1) from a mixture resulted from the reaction of converting(+)-Corey diol to the compound of formula (M1) by crystallization.

13. A process for preparing a compound of formula

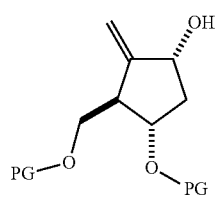
M5 comprising:
oxidizing a compound of formula (M2):

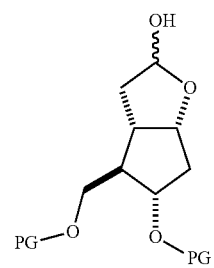
M2 to provide an intermediate of formula (IM1):

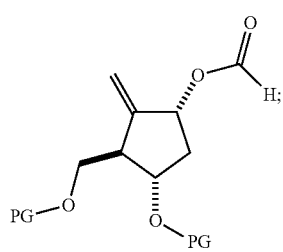
IM1 and
hydrolyzing the intermediate of formula (IM1) to the compound of formula (M5);

wherein the two PGs on the formula (IM1), (M2) and (M5) are taken together with the two oxygen atoms and the carbon atoms between the two oxygen atoms to form an optionally substituted six- or seven-member ring.

14. The process of claim 13 wherein the step of oxidizing and the step of hydrolyzing are carried out in one pot.

15. The process of claim 13 wherein the oxidizing step is carried out in the presence of an oxidizing agent selected from the group consisting of $Pb(OAc)_4/CuCl_2$, $PhI(OAc)_2$ (iodobenzene diacetate)/$CuCl_2$, $Pb(OAc)_4/CuBr_2$, $PhI(OAc)_2/CuBr_2$, $Pb(OAc)_4/CuI_2$, $PhI(OAc)_2/CuI_2$, $Pb(OAc)_4/CuSO_4$, $PhI(OAc)_2/CuSO_4$, $I_2$/AIBN, $PbI(OAc)_2/I_2$/AIBN, $Mn(OAc)_3$, ceric ammonium nitrate (CAN), $Fe(OAc)_3$, $PhI(OAc)_2$, Dess-Martin periodinane (DMP), 2-Iodoxybenzoic acid (IBX), and combinations thereof.

16. A compound of formula (IM1):

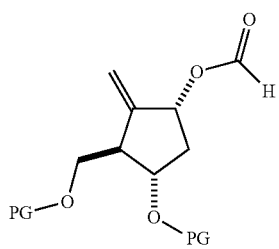
IM1 wherein each of the PGs is independently a hydroxy protecting group, or taken together with the two oxygen atoms to which they attach and the carbon atoms between the two oxygen atoms to form an optionally substituted six- or seven-member ring.

17. A compound with one of the following formulae:

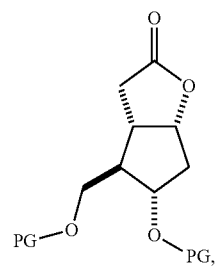
M1

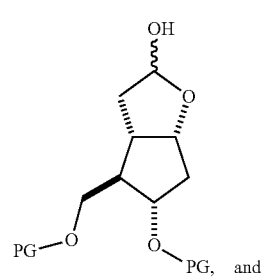
M2

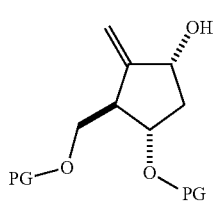
M5
wherein the two PGs on the formulae (M1), (M2) and (M5) are taken together with the two oxygen atoms to which they attach and the carbon atoms between the two oxygen atoms to form an optionally substituted six- or seven-member ring.
* * * * *